United States Patent
Dinsmoor et al.

(10) Patent No.: US 10,080,902 B2
(45) Date of Patent: *Sep. 25, 2018

(54) IMPLANTABLE MEDICAL DEVICES AND SYSTEMS HAVING INDUCTIVE TELEMETRY AND RECHARGE ON A SINGLE COIL

(71) Applicant: MEDTRONIC, INC., Minneapolis, MN (US)

(72) Inventors: David A. Dinsmoor, St. Paul, MN (US); Joel A. Anderson, Brooklyn Park, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/594,543

(22) Filed: May 12, 2017

(65) Prior Publication Data

US 2017/0326374 A1 Nov. 16, 2017

Related U.S. Application Data

(60) Continuation of application No. 14/820,568, filed on Aug. 7, 2015, now Pat. No. 9,653,941, which is a division of application No. 13/096,073, filed on Apr. 28, 2011, now Pat. No. 9,136,728.

(51) Int. Cl.
| | |
|---|---|
| *H02J 7/00* | (2006.01) |
| *A61N 1/372* | (2006.01) |
| *A61N 1/378* | (2006.01) |
| *H02J 7/02* | (2016.01) |
| *H02J 50/10* | (2016.01) |

(52) U.S. Cl.
CPC ....... *A61N 1/37223* (2013.01); *A61N 1/3787* (2013.01); *H02J 7/025* (2013.01); *H02J 50/10* (2016.02)

(58) Field of Classification Search
CPC ...................................................... H02J 7/027
USPC ........................................................ 320/108
See application file for complete search history.

(56) References Cited

U.S. PATENT DOCUMENTS

| | | | |
|---|---|---|---|
| 6,456,883 B1 * | 9/2002 | Torgerson | A61N 1/08 607/32 |
| 6,549,807 B1 * | 4/2003 | Kroll | A61N 1/3956 607/34 |
| 7,177,698 B2 * | 2/2007 | Klosterman | A61N 1/37205 607/60 |

(Continued)

*Primary Examiner* — Yalkew Fantu
(74) *Attorney, Agent, or Firm* — Withers & Keys, LLC

(57) ABSTRACT

Implantable devices and related systems utilize a single coil for both inductive telemetry at one telemetry signal frequency and recharge at another recharge energy frequency. The coil is included in a tank circuit that may have a variable reactance. During telemetry, particularly outside of a recharge period, the reactance may be set so that the tank circuit is tuned to the telemetry frequency. During recharge, the reactance is set so that the tank circuit is tuned to the recharge frequency. Furthermore, the tank circuit may have a Q that is sufficiently small that the tank circuit receives telemetry frequency signals that can be decoded by a receiver while the tank is tuned to the recharge frequency so that telemetry for recharge status purposes may be done during the recharge period without changing the tuning of the tank circuit.

20 Claims, 25 Drawing Sheets

(56) References Cited

U.S. PATENT DOCUMENTS

| | | | |
|---|---|---|---|
| 2002/0177884 A1* | 11/2002 | Ahn | A61N 1/3787 607/61 |
| 2005/0075693 A1* | 4/2005 | Toy | A61N 1/37211 607/60 |
| 2007/0060967 A1* | 3/2007 | Strother | A61N 1/08 607/31 |
| 2010/0137948 A1* | 6/2010 | Aghassian | A61N 1/3787 607/61 |

* cited by examiner

IMPLANTABLE MEDICAL DEVICES AND SYSTEMS HAVING INDUCTIVE TELEMETRY AND RECHARGE ON A SINGLE COIL

TECHNICAL FIELD

Embodiments relate to implantable medical devices that utilize inductive couplings for telemetry and for recharge at one or more frequencies. More particularly, embodiments relate to implantable medical devices that use a shared coil for the telemetry and recharge applications.

BACKGROUND

Implantable medical devices (IMD) may provide a variety of different therapies and other functions including stimulation, drug infusion, physiological sensing, and the like. The IMDs receive programming from an external device and may also share information that has been collected with the external device. Many IMDs communicate with the external device using an inductive form of telemetry where a telemetry head is held in communication range of the IMD so that inductive signals may be exchanged.

The inductive downlink is obtained by a coil within the IMD that is tuned to a telemetry frequency, e.g., 175 kilohertz, being emitted by a coil within the external device. Likewise, the inductive uplink is provided by a coil within the IMD that is tuned to emit signals at a telemetry frequency of the coil of the external device. The uplink and downlink telemetry frequencies are frequently the same and a single coil in each device is tuned to a single frequency that is used for both the uplink and the downlink.

Many IMDs operate on power from a battery, capacitor, or similar power source and therefore have a limited lifetime of operation before a replacement or a recharge is necessary. For IMDs with a rechargeable power source, the recharge energy may be received via an inductive coupling. The external device has a coil tuned to a recharge frequency, e.g., 100 kilohertz, which may differ from the telemetry frequency. Many commercially available IMDs have a second coil that is tuned to the recharge frequency being emitted by the external device.

While using two coils with the 1 MB adequately establishes telemetry and recharge applications, the size occupied by two separate coils restricts the ability to make smaller IMDs. Thus, miniaturized 1 MB designs call for a single coil such that the inclusion of the telemetry application precludes inclusion of the recharge application.

SUMMARY

Embodiments address issues such as these and others by providing IMDs that may include a single coil used for both telemetry and recharge applications. At least for some exchanges of information by telemetry, the IMD may utilize a tank circuit tuned to a recharge frequency of recharge energy to send and/or receive telemetry signals at a telemetry frequency that is different than the recharge frequency.

Embodiments provide an implantable medical device that includes a tank circuit tuned to a recharge frequency of recharge energy. The implantable medical device includes a receiver with at least one input electrically connected to a node of the tank circuit, the receiver being configured to receive telemetry signals at a telemetry frequency while the tank circuit is tuned to the recharge frequency. The implantable medical device includes a rechargeable power source and a rectifier that is electrically connected between the rechargeable power source and the tank circuit and that is configured to receive the recharge energy at the recharge frequency. The implantable medical device also includes medical circuitry electrically connected to the rechargeable power source.

Embodiments provide an implantable medical device that includes a tank circuit tuned to a recharge frequency of recharge energy. The implantable medical device includes a driver circuit electrically connected to a node of the tank circuit, the driver circuit being configured to produce telemetry signals at a telemetry frequency while the tank circuit is tuned to the recharge frequency. The implantable medical device includes a rechargeable power source and a rectifier that is electrically connected between the rechargeable power source and the tank circuit and is configured to receive the recharge energy at the recharge frequency. The implantable medical device includes medical circuitry electrically connected to the rechargeable power source.

Embodiments provide an external recharge device that includes a tank circuit tuned to a recharge frequency of recharge energy. The external recharge device further includes a receiver with at least one input electrically connected to a node of the tank circuit, the receiver being configured to receive from the tank circuit incoming telemetry signals at a telemetry frequency. The external recharge device further includes a driver circuit electrically connected to a node of the tank circuit. Additionally, the external recharge device includes a controller in electrical communication with the driver circuit, the controller causing the driver circuit to drive the tank circuit at the recharge frequency when sending recharge energy and to drive the tank circuit at a telemetry frequency when sending outbound telemetry signals.

Embodiments provide a medical system that includes an external recharge device that transmits recharge energy at a recharge frequency from a tank circuit tuned to the recharge frequency and that exchanges telemetry signals at a telemetry frequency that is different than the recharge frequency through the tank circuit tuned to the recharge frequency. The medical system further includes an implantable medical device that receives recharge energy at the recharge frequency from a tank circuit tuned to the recharge frequency and that exchanges telemetry signals at the telemetry frequency through the tank circuit tuned to the recharge frequency.

Embodiments provide a method of interaction with an implantable medical device. The method involves, at the implantable medical device, receiving recharge energy at a recharge frequency from a tank circuit of the implantable medical device that is tuned to the recharge frequency. The method further involves, at the implantable medical device, exchanging telemetry signals at a telemetry frequency through the tank circuit of the implantable medical device that is tuned to the recharge frequency.

DETAILED DESCRIPTION

Embodiments provide for medical systems including IMDs that offer both inductive telemetry and recharge applications using a single coil. The telemetry may include uplink, downlink, or both, and various configurations for the telemetry may be provided with the single coil. Likewise, various configurations may be provided for the recharge application, including various rectifier and power management approaches, while using the single coil.

Figure 1:
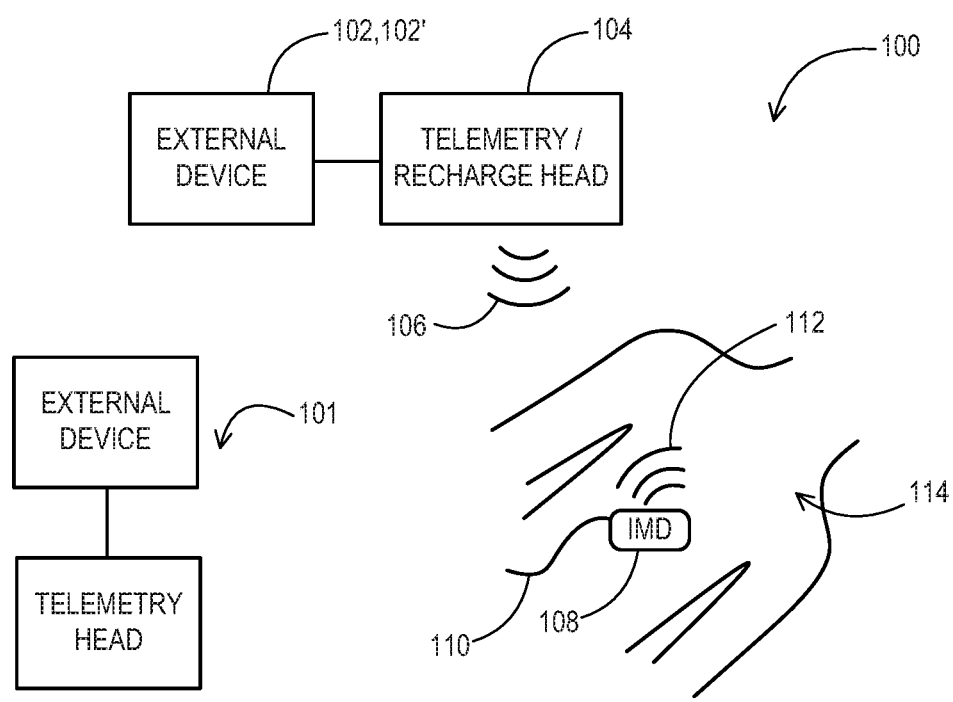
FIG. 1 shows a typical operating environment for a medical system including an external device and an IMD according to various embodiments.

FIG. 1 shows a typical operating environment for a medical system 100 that includes an external device 102 and an IMD 108. The external device 102 may provide programming and data collection services by using inductive telemetry. The external device 102 may also provide recharge services by using an inductive coupling. A telemetry/recharge head 104 that is tethered to the external device 102 may be placed nearby the patient's body 114 and in communication range of the IMD 108 so that an inductive coupling occurs between a coil within the head 104 and the coil within the IMD 108.

The head 104 may emit inductive signals 106 that represent downlink telemetry signals or recharge signals. The telemetry signals are emitted at one frequency while the recharge signals are emitted at a different time and at another frequency. For instance, the telemetry signals may be 175 kilohertz while the recharge signals are at 100 kilohertz. However, many different frequencies are possible for both telemetry and recharge and the recharge frequency may either be of a higher or lower frequency than the telemetry. While a single external device 102 is shown for both telemetry and recharge applications, it will be appreciated that these applications may be provided by different external devices where a first external device conducts a telemetry session at the telemetry frequency and a second external device conducts a recharge session at the recharge frequency at some other time.

Furthermore, in some cases, one external device 102' may provide a recharge function and may also provide a telemetry function that operates during a period of time when recharge is also being conducted with pauses in the recharge while the telemetry takes place such as to convey recharge status. In such cases, another external device 101 may be present at other times to carry on a telemetry session for other purposes than recharge status, such as to program the IMD 108.

Embodiments of the IMD 108 may utilize the same coil for the downlink and for the recharge. In such embodiments, the IMD 108 receives the inductive signals 106, including both the telemetry and the recharge signals, on the coil. Embodiments of the IMD 108 may additionally or alternatively utilize the same coil for the uplink and for the recharge. In such embodiments, the IMD 108 emits inductive telemetry signals 112 from the coil, and those signals are received by the coil of the head 104.

The IMD 108 of this example includes an extension 110 such as a medical lead or a catheter that allows the IMD 108 to perform one or more medical functions. For instance, where the extension 110 is a medical lead, then IMD 108 may provide stimulation signals to the body 114 via electrodes on the lead and/or may sense physiological signals of the body 114 via the electrodes. Where the extension 110 is a catheter, the IMD 108 may infuse drugs into the body 114. These medical functions may be performed by the IMD 108 in accordance with programming received via the inductive telemetry signals and may be performed by using power from a rechargeable power source such as a battery or capacitor that is replenished by the inductive recharge signals. While a battery is discussed below for purposes of illustration in relation to the several embodiments, it will be appreciated that the embodiments may include other rechargeable power sources in addition to or as an alternative to a battery.

Figure 2A:
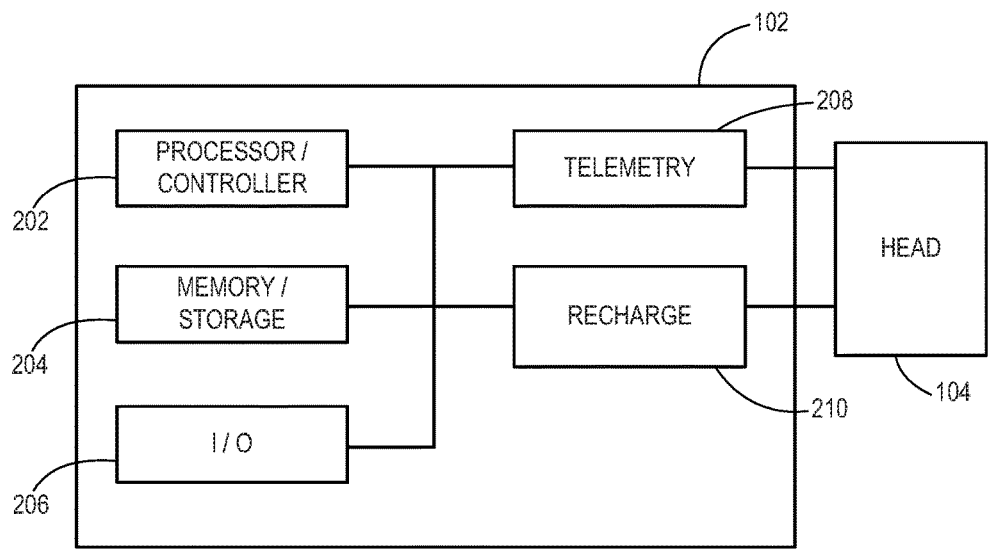
FIG. 2A shows a diagram of components of an example of an external device.

FIG. 2A shows components of one example of the external device 102. The external device 102 includes a processor/controller 202 and memory/storage device(s) 204. The external device 102 may also include local input/output (I/O) ports 206 such as to provide local screen displays and to receive user input via keyboard, mouse, and so forth. The external device 102 also includes a telemetry module 208 used to establish the telemetry to the IMD 108, and the telemetry module 208 may provide signals at the telemetry frequency to the head 104 during telemetry sessions. The external device of this example also includes a recharge module 210 used to transfer recharge energy to the IMD 108, and the recharge module 210 may provide signals at the recharge frequency to the head 104 during recharge sessions.

The memory/storage devices 204 may be used to store information in use by the processor 202. For instance, the memory/storage 204 may store therapy parameters that are input by a clinician or patient that are to be downlinked into the IMD 104. The memory/storage devices 204 may also store programming that is used by the processor 202 to control the telemetry and recharge actions of the external device 102. The memory/storage devices 204 may be of various types, such as volatile, non-volatile, or a combination of the two. The memory storage devices 204 may be used to store information for a long term and may be of various types such as electronic, magnetic, and optical drives. The memory/storage devices 204 are examples of computer readable media that may store information in the form of computer programming, data structures, and the like.

The processor/controller 202 includes logic to perform various operations to allow telemetry and/or recharge sessions with the IMD 108. The processor/controller 202 may be of various forms. For instance, the processor/controller 202 may include a general-purpose programmable processor that executes software that is stored on the memory/storage devices 204 or elsewhere. Other examples include a dedicated purpose hardware circuit or hard-wired digital logic. The processor/controller 202 may communicate with the various other components through one or more data buses.

The external recharge device 102 may include multiple tank circuits, each tank circuit having a coil with each tank circuit having a dedicated purpose and frequency. For instance, one tank circuit may be for telemetry at a first frequency such as 175 kHz while another tank circuit may be for recharge at a second frequency such as 100 kHz. In such a case, both coils of the tank circuits may be present within a common enclosure so that the patient need only manipulate a single enclosure in proximity to the IMD 108 to enable both telemetry and recharge. As an alternative, the external recharge device 102 may include a single tank circuit and coil where the tank circuit may be tuned to the appropriate frequency of the signal being sent or received at any given moment.

For some embodiments, the external recharge device 102 may send and receive telemetry signals that are during a period of recharge. So, while the tank circuit may be tuned to the recharge frequency for optimal recharge coupling, the external device 102 may periodically pause the recharge in order to exchange telemetry signals related to the recharge status. In one embodiment, the external recharge device 102 may utilize a dedicated telemetry tank circuit for the telemetry if so equipped. In another embodiment that includes a single tank circuit, the external recharge device 102 may tune the tank circuit to the telemetry frequency if the external recharge device 102 is equipped to tune the tank circuit.

Figure 2B:
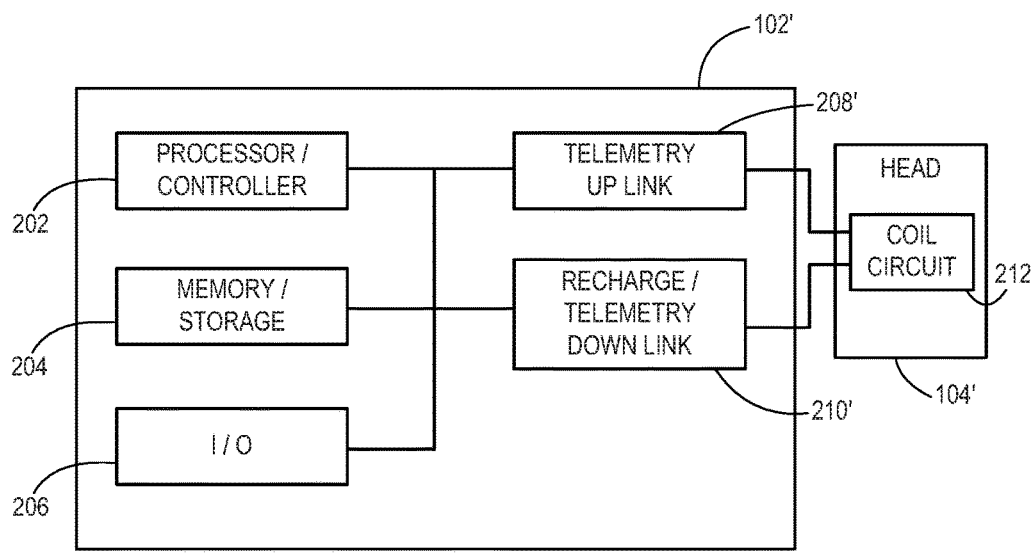
FIG. 2B shows a diagram of components of an example of an external device that utilizes a shared coil for recharge and telemetry.

In yet another embodiment, the external recharge device 102' as shown in FIG. 2B may include the same components as the external recharger device 102 above except that this external recharger device 102' may be simplified by having within the head 104' a coil circuit 212 that includes the single tank circuit with fixed tuning. The single tank circuit may have fixed tuning, for instance tuned to the recharge frequency even though the external recharge device 102' may communicate via telemetry signals with the IMD 108 such as during a period of recharge. The telemetry uplink circuit 208' includes a receiver while a recharge/telemetry downlink circuit 210' includes a driver that may drive the tank circuit at either the recharge frequency for recharge purposes or the telemetry frequency for telemetry purposes. Additional details for the construction of this example of an external recharger device 102' are discussed in more detail below with respect to FIGS. 25 and 26.

This embodiment in FIG. 2B may have a relatively high Q tank circuit, such as a Q of about 200 for example which is beneficial for transmitting recharge energy and/or telemetry signals. However, as discussed below in relation to FIG. 25, the external recharger may include the ability to de-Q the tank circuit by adding impedance during reception of telemetry signals to widen the bandwidth which allows the tank circuit to adequately couple at a telemetry frequency that differs from the tuned frequency. For example, the tank circuit may adequately couple with a coil of an IMD 108 at a telemetry frequency of 175 kHz while the tank circuit of the external recharge device 102' is tuned to 100 kHz. This allows the external recharge device 102' to have a relatively simple construction while being able to exchange telemetry signals with the IMD 108 during a period of recharge without the need to configure telemetry via a different coil or via a change of tuning of the single coil. This in turn reduces the amount of time to exchange the telemetry signals and thereby reduces the amount of time needed to complete a recharge of the IMD 108.

Figure 2C:
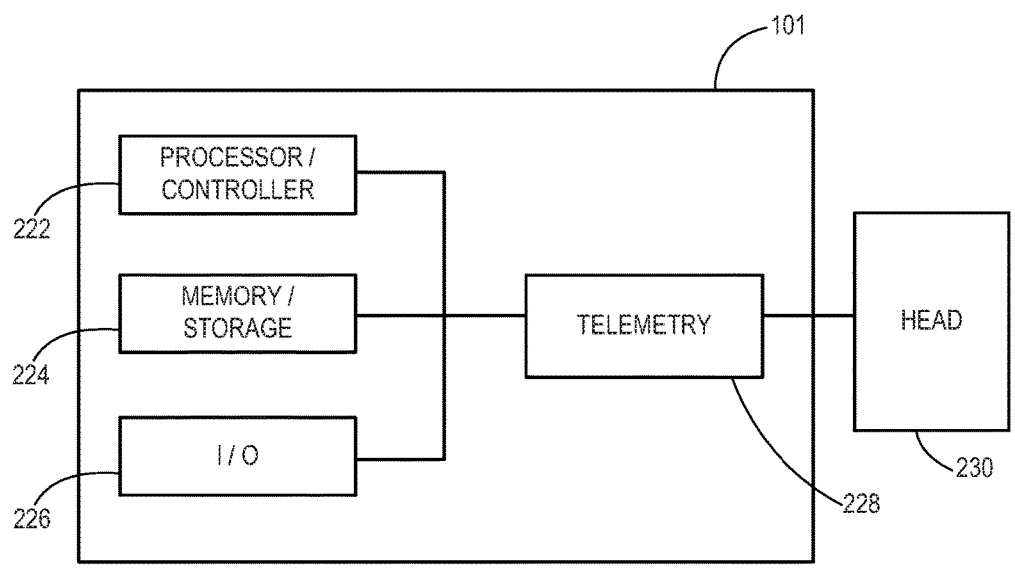
FIG. 2C shows a diagram of components of an example of an external device that interacts with the IMD via telemetry but does not perform recharge.

FIG. 2C shows an example of the external telemetry device 101 that is used to communicate via telemetry signals with the IMD 108 at times other than during a recharge period. The external telemetry device 101 may include some of the same components as the external recharger device 102 above, including a controller 222, memory and storage 224, I/O 226, and a telemetry circuit 228. This external telemetry device 102 may omit the ability to provide recharge energy such as by being configured to drive a tank circuit having a coil within the head 230 at only the telemetry frequency.

Figure 3:
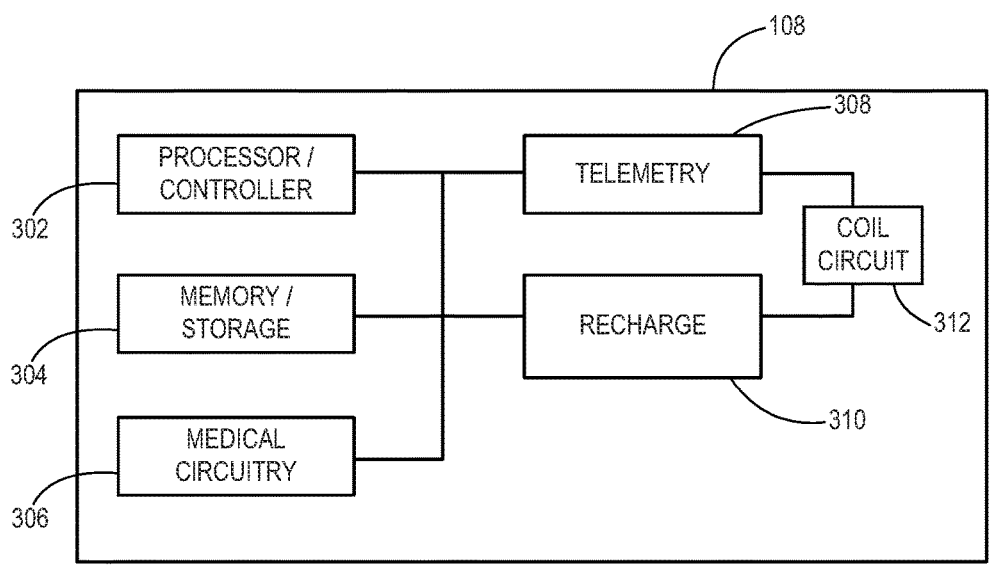
FIG. 3 shows a diagram of components of an example of an IMD.

FIG. 3 shows components of one example of the IMD 108. The IMD 108 includes a processor/controller 302 and a memory/storage device(s) 304. The IMD 108 also includes medical circuitry 306 that performs a medical task such as stimulation, drug delivery, monitoring, and the like. The IMD 108 also includes telemetry circuitry 308 used to establish the uplink and/or downlink telemetry with the external device 102 in conjunction with single coil circuitry 312. The IMD 108 further includes recharge circuitry 310 used to receive recharge energy from the external device 102 in conjunction with the single coil circuitry 312.

The memory/storage devices 304 may be used to store information in use by the processor/controller 302 such as programming and data values. The memory/storage devices 304 may store additional information including therapy parameters that are used to control the medical circuitry 306. The memory/storage devices 304 may be of various types such as volatile, non-volatile, or a combination of the two. The memory/storage devices 304 are also an example of computer readable media that may store information in the form of computer programming, data structures, and the like.

The processor/controller 302 includes logic to perform operations that allow telemetry and recharge sessions with the external device 102 to be established. The processor/controller 302 may be of various forms like those discussed above for the processor/controller 202 of the external device 102, such as a general purpose processor, an application specific circuit, hardwired digital logic, and the like. The processor/controller 302 may communicate with the various other components through one or more data buses. The processor/controller 302 may also control silicon based switches that are either integral to the processor/controller 302 or separate electronic devices to provide the telemetry, recharge, and power management functions while using the single coil. These switches and other circuit details are discussed in more detail below with reference to FIGS. 4-24.

For some embodiments, the IMD 108 may send and receive telemetry signals during a period of recharge. So, while the tank circuit may be tuned to the recharge frequency for optimal recharge coupling to the external recharge device, the IMD 108 may listen for and periodically exchange telemetry signals related to the recharge status such as in response to a request by the external recharge device. In one embodiment that includes a single tank circuit, the IMD 108 may tune the tank circuit to the telemetry frequency.

In yet another embodiment, the IMD 108 may maintain the tuning for both recharge energy and telemetry during a recharge period. For instance, the tank circuit of the IMD 108 may be tuned to the recharge frequency even though the IMD 108 may communicate via telemetry signals with the external recharge device during a period of recharge.

In contrast to the external recharge device 102', embodiments of the IMD 108 may rely on a relatively low Q tank circuit, such as for example a Q in the range of 2 to 6 that may be achieved by the interaction of the coil of the tank circuit and the metal or other conductive material of the enclosure of the IMD 108 that includes the coil. As a specific example, with a hermetically sealed, titanium shell, the Q of a 500 µH coil within a ~3 cc IMD 108 with 0.008" Grade-5 Titanium shields is approximately 3. This relatively low Q provides a wide bandwidth and allows the tank circuit to adequately couple at a telemetry frequency that differs from the tuned frequency. For example, the tank circuit may adequately couple with a coil of an external recharge device at a telemetry frequency of 175 kHz while the tank circuit of the IMD 108 is tuned to 100 kHz. This allows the IMD 108 to exchange telemetry signals with the external recharge device during a period of recharge without the need to configure telemetry via a different coil or via a change of tuning of the single coil. This in turn reduces the amount of time to exchange the telemetry signals and thereby reduces the amount of time needed to complete a recharge.

In an application where the recharge frequency is 100 kHz and the telemetry frequency is 175 kHz, a receiver of the telemetry circuitry 308 with suitable out-of-band aggressor performance, utilizing synchronous demodulation for instance, may detect a coupled 175 kHz telemetry signal on a 100 kHz tuned coil, especially if the signal is large due to good coupling and/or a large signal on the primary. In the same example, the H-bridge circuit may be used to drive the tank at 175 kHz. This signal may in turn be sensed by a receiver of the external recharge device 102' discussed above which also possesses sufficient sensitivity and frequency selectivity.

The converse is also true. If the tank circuit is tuned to the telemetry frequency of 175 kHz, recharge energy at 100 kHz may be still be coupled onto the coil of the tank circuit within the IMD 108 and flow through a rectifier to recharge the battery or other rechargeable power source. Thus, in some embodiments, the external device 100 may be configured to emit 100 kHz energy via a tank circuit tuned to 175 kHz in certain situations such as when the IMD 108 has a low battery and a recharge device 102, 102' is not available. In that case, the IMD 108 being tuned to 175 kHz receives the 100 kHz energy to provide some degree of recharge which may then allow the external device 101 to subsequently communicate with the IMD 108 without the IMD 108 reaching a depleted battery condition.

Figure 4:
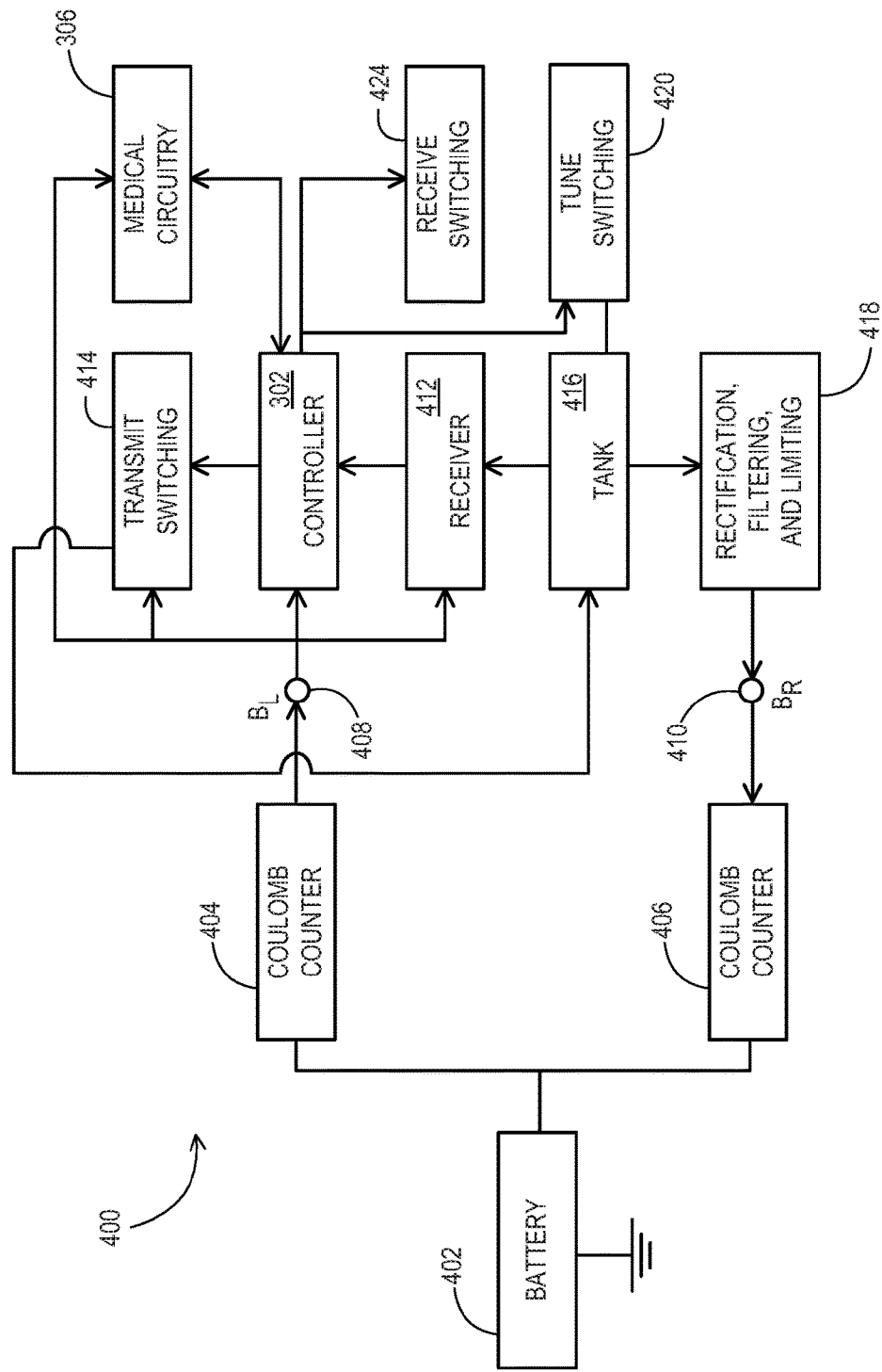
FIG. 4 shows a diagram of a load branch and a recharge branch of an example of an IMD.

FIG. 4 shows one example of a configuration 400 of circuit modules that may be employed in various embodiments of the IMD 108. This configuration 400 includes a battery 402 that provides the energy for the general operation of the IMD 108 including the operations being performed by the logic of the processor/controller 302 and the medical tasks being performed by the medical circuitry 306. The battery 402 also receives the energy being collected during the recharge session.

As shown, there is a load branch stemming from a node 408 and a recharge branch stemming from a node 410, where the node 408 and node 410 stem from the battery 402. In this example, each branch includes a Coulomb counter, 404, 406 where the Coulomb counter 404 for the load branch measures the amount of charge leaving the battery while the Coulomb counter 406 for the recharge branch measures the amount of charge entering the battery. The processor/controller 302 may gather this information to monitor the condition of the battery 402 as well as to report such information to the external device 102.

The node 408 sources power to several components. The processor/controller 302 receives power to operate including implementing the logic and output to control various switches that vary the tuning frequency of the coil and select between uplink, downlink, and recharge modes. Drive circuitry such as an oscillator, for instance a sinusoidal power amplifier, or such as a set of transmitter switches 414 receive power to ultimately ring the coil to emit telemetry signals. A receiver 412 consumes power to receive and amplify the downlink telemetry signal and return it to the controller 302. The medical circuitry 306 receives power to perform the medical tasks such as pulse generation, drug infusion, data collection, and the like.

Several components receive control signals from the processor/controller 302. The drive circuitry 414 may receive an activation signal in the case of an oscillator. The drive circuitry may receive timed control signals, discussed in more detail below with reference to FIGS. 20 and 21, in the case of transmitter switches that alternate their states in order to ring the coil at the telemetry frequency to uplink telemetry signals. A set of receiver switches 424 receive control signals to achieve a state that allows detection of the telemetry signal of the coil at the receiver 412. A tuning switch 420 receives a control signal to alter the state and ultimately vary the reactance of a tank circuit 416 that includes the coil so that one state tunes the tank circuit 416 to a telemetry frequency while another state tunes the tank circuit 416 to a recharge frequency.

The node 410 of the recharge branch receives power from a power module 418. This power module 418 receives the recharge signal induced onto the coil of the tank circuit 416 by the incoming recharge signals. The power module 418 includes a rectifier, a filter, and a limiter so that the node 410 receives power that has a suitable voltage and current for recharging the battery 402.

The various switching modules of FIG. 4 have a default state such as where no control signal is present either by operation of the processor/controller 302 or as a result of a fully depleted battery 402. One configuration of the switches is such that when all switches are in the default state, the tank circuit 416 is tuned to the telemetry frequency with the tank circuit's output being directed into the rectifier of the power module 418. Thus, an attempt at communicating with the IMD 108 that is currently non-operational via telemetry may succeed in supplying enough recharge energy to the battery 402 to allow the processor/controller 302 to become operational and respond.

Figure 5:
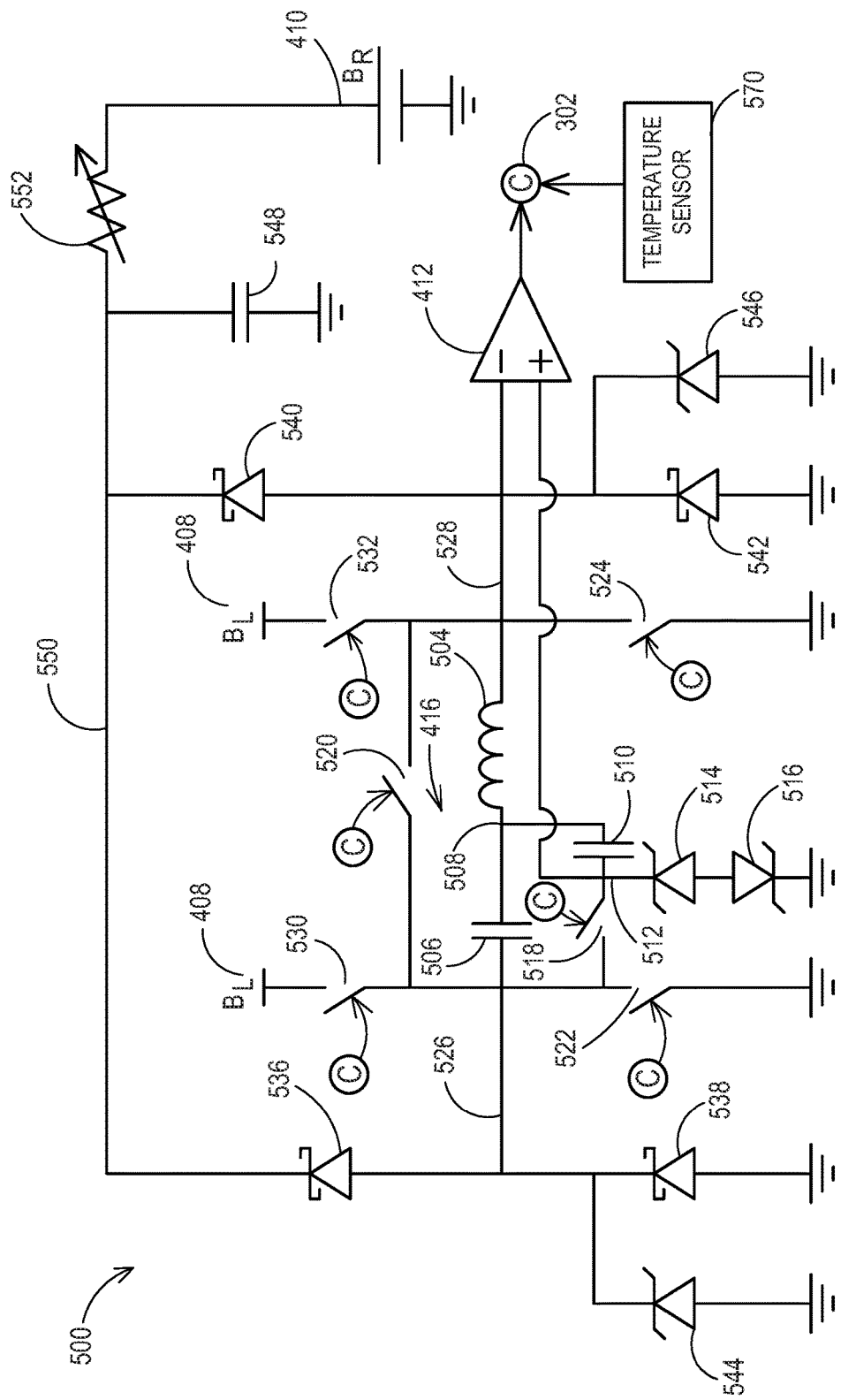
FIG. 5 shows a circuit of one example of an IMD that provides for telemetry uplink and telemetry downlink and recharge with a single coil and with a first receiver configuration and a first rectifier configuration.

Examples of specific circuits such as those that are shown in FIGS. 5-19 and 22-24 and others that are discussed below implement the modules of FIG. 4 while providing the default state that allows for recharge at the telemetry frequency. FIG. 5 shows a first configuration 500 for a circuit that provides for telemetry uplink and downlink at a telemetry frequency with the tank circuit tuned to the telemetry frequency such as to allow for arm's length coupling. The configuration 500 also provides for recharge with power management at a recharge frequency that is different than the telemetry frequency with the tank circuit tuned to the recharge frequency while using a single coil. Additionally, the first configuration 500 allows for telemetry uplink and downlink at the telemetry frequency during a recharge period while the tank circuit remains tuned to the recharge frequency. As discussed above, the first configuration 500 includes switches implemented in silicon with a default state that is open which allows for recharge mode to occur at the telemetry frequency when the IMD 108 is non-operational due to a depleted battery.

The first configuration includes the tank circuit 416 that has a coil 504 and the variable reactance is provided by a variable capacitance. The variable capacitance is achieved in this example by providing a first capacitor 506 that is hardwired in series with the coil 504 and by providing a second capacitor 510 that is switched into and out of a parallel relationship with the first capacitor 506 by a tuning switch 518, which is implemented in silicon and is under the control of the processor/controller 302. The processor/controller 302 may open and close the tuning switch 518 to vary the capacitance of the tank circuit and thereby tune the resonant frequency of the tank circuit 416 to either the telemetry or the recharge frequency.

In this particular example, the telemetry frequency is higher than the recharge frequency and so the coil 504 is tuned to the telemetry frequency when less capacitance is present. It will be appreciated that the opposite design could be employed where the recharge frequency is higher and thus some capacitance is switched out of the circuit to tune the coil 504 to the recharge frequency.

The tank circuit 416 establishes several nodes. An inductor side node 528, a capacitor side node 526, and a high voltage node 508 are achieved. The high voltage node 508 acquires a relatively high voltage periodically as the voltage swings within the tank circuit 416. An additional capacitor side node 512 is present particularly when the tuning switch 518 is open.

The capacitor side node 526 and inductor side node 528 are connected to a rectifier that is established by a set of diodes 536, 538, 540, and 542 that may be of the Schottky variety. These diodes form a full-bridge rectifier. However, a capacitor low side switch 522 and an inductor low side switch 524 are present and either one may be closed by the processor/controller 302 to provide a half-wave rectifier.

As an alternative rectifier for this configuration, the capacitor low side switch 522 and the inductor low side switch 524 may be operated as low-side synchronous rectifier switches. In such a case, the state machine control of these switches 522, 524 by the processor/controller 302 operates by closing the capacitor low side switch 522 while leaving the inductor low side switch 524 open when the inductor side node 528 flies high and by closing the inductor low side switch 524 while leaving the capacitor low side switch 522 open when the capacitor side node 526 flies high. Other rectifier options are discussed with reference to other circuit diagrams below.

A capacitor side Zener diode 544 and an inductor side Zener diode 546 are also present. These devices limit voltage swings on the capacitor side node 526 and the inductor side node 528 to prevent over-voltage damage from occurring on voltage sensitive devices connected to these nodes. Voltage sensitive devices may include the various switches which are implemented in silicon and particularly those that are implemented as monolithic devices. Likewise, Zener diodes 514 and 516, shown in an anode-to-anode relationship but could be in a cathode-to-cathode relationship, are present to prevent over-voltage damage from occurring on additional voltage sensitive devices such as the tuning switch 518 on the additional capacitor side node 512. These devices may be actual Zener diodes or may be other devices which have Zener-like behavior.

The high voltage node 508 achieves the highest voltage during voltage swings within the tank circuit 416. As can be seen, no voltage sensitive device is DC coupled to the high voltage node which reduces the likelihood of any damage to those voltage sensitive devices. While the additional capacitor side node 512 may also achieve the relatively high voltage during telemetry by being AC coupled to the high voltage node 508 via the second capacitor 510 while the turning switch 518 is open, the Zener diodes 514, 516 provide additional protection for the tuning switch 518.

The rectifier provides voltage to a rectifier recharge node 550. This rectifier recharge node 550 also includes a filtering capacitor 548 in parallel with the rectifier. A current or voltage limiter 552 is in series between the rectifier recharge node 550 and the battery recharge node 410 to prevent the battery 402 from receiving voltage and/or current in excess of the amounts rated for the battery 402.

This embodiment of the IMD 108 is also capable of telemetry downlink by using the tank circuit 416. The receiver 412 is present to receive the telemetry signals induced on the coil 504. The receiver 412 is connected to the tank circuit in a first configuration in the example of FIG. 5. Other configurations are discussed below with reference to other figures. In this example, a first input of the receiver 412 is connected to the inductor side node 528 while a second input of the receiver 412 is connected to the additional capacitor side node 512. In this manner the second input of the receiver 412 is capacitively coupled to the high voltage node 508 via the second capacitor 510 regardless of the state of the tuning switch 518. As the input impedance of the receiver 412 is very high, the receiver 412 does not appreciably affect the tuning of the tank circuit 416.

A tank switch 520 is included between the capacitor side node 526 and the inductor side node 528. This tank switch 520 when closed can effectively bypass the rectifier during the downlink telemetry. Other options for downlink telemetry where the tank switch 520 is left open or omitted are discussed below in relation to other figures.

This embodiment of the IMD 108 is also capable of telemetry uplink by using the tank circuit 416 and one of various methods. For instance, as shown, an H-bridge may be provided in relation to the tank circuit 416 by connecting a capacitor high side switch 530 between the load node 408 and the capacitor side node 526 while also connecting an inductor high side switch 532 between the load node 408 and the inductor side node 528.

The various modes of operation of the configuration 500 operate as follows. During recharge mode when using full wave rectification, the processor/controller 302 of this example sets the tuning switch 518 to the state that provides the proper capacitance for setting the resonant frequency of the tank circuit 416 to the recharge frequency. All other switches remain open. As a result, the current of the tank circuit passes through the rectifier and on to the limiter and ultimately to the battery 402. If half wave rectification is desired, then either capacitor low side switch 522 or inductor low side switch 524 is closed.

During recharge, one concern is that in an overcharge condition, the limiter 552 increases impedance which pumps up voltage on the rectifier recharge node 550 to a Schottky drop below the peak voltage on the capacitor side node 526 and inductor side node 528. The peak voltage on these two nodes is set by the Zener diodes 544, 546. If a large amount of energy continues to be coupled into the coil 504, then the Zener diodes 544, 546 may be subjected to significant heating which can be problematic.

In such a case, the processor/controller 302 may detect such heating or overcharge via a temperature sensor 570 or other measurement device and respond in various ways. For instance, the processor/controller 302 may change the state of the tuning switch 518 so that the coupling coefficient between the coil 504 and the coil of the external device 102 is decreased, thereby decreasing the power being received. Additionally or alternatively, the processor/controller 302 may close the capacitor low side switch 522 and the inductor low side switch 524 to clamp the tank circuit 416 to ground, as the coil 504, capacitors 506, 510, and Zener diodes 514, 516 together may be better suited to dissipate the heat as part of the larger system.

During telemetry downlink, where tuning to the telemetry frequency is desired such as to establish an arm's length coupling at a time other than a recharge period, the processor/controller 302 of this example sets the tuning switch 518 to the opposite state from that set for recharge so that the proper capacitance for setting the resonant frequency of the tank circuit 416 to the telemetry frequency is achieved. The tank switch 520 is then closed. All other switches are left open, and the capacitor side node 526 and the inductor side node 528 are allowed to float within a diode drop below ground and above rectifier recharge node 550, respectively. The receiver 412 picks up the differential voltage across the coil 504. Several other methods of telemetry downlink are discussed below with reference to other circuit diagrams.

During telemetry downlink where the tuning may remain at the recharge frequency, such as during a recharge period, the processor/controller 302 of this example may maintain the tuning switch 518 in the same state that is used for recharge so that the proper capacitance for setting the resonant frequency of the tank circuit 416 to the recharge frequency is maintained. The tank switch 520 is then closed. All other switches are left open, and the capacitor side node 526 and the inductor side node 528 are allowed to float within a diode drop below ground and above rectifier recharge node 550, respectively. The receiver 412 picks up the differential voltage across the coil 504 even though the tank circuit 416 continues to be tuned to the recharge frequency. Furthermore, the telemetry signals may be rectified to continue to provide some degree of recharge energy to the battery.

Maintaining the recharge switch in a closed state during downlink telemetry limits high-voltage excursions on the high voltage node 508, which in turn limits the potential seen on the cathode of the Zener diode 514 which is AC coupled to high voltage node 508 via the recharge capacitor 510. When the tuning switch 518 is closed, the potential on the cathode of the Zener diode 514 is limited to a diode drop below ground and a diode drop above the voltage on the rectifier recharge node 550. As such, there is no potential for anode connected Zener diodes 514, 516 to activate, which is beneficial as Zener diodes 514, 516 are only intended to operate occasionally.

During telemetry uplink, where tuning to the telemetry frequency is desired such as to establish an arm's length coupling at a time other than a recharge period, the tuning switch 518 is set to tune the tank circuit 416 to the telemetry frequency. The H-bridge may be operated by opening the capacitor high side switch 530 and the inductor low side switch 524 while the inductor high side switch 532 and the capacitor low side switch 522 are closed. After a set amount of time defined by the telemetry frequency, the inductor high side switch 532 and the capacitor low side switch 522 are opened while the capacitor high side switch 530 and the inductor low side switch 524 are closed. These pairings continue to alternate states to ring up the coil 504 at the telemetry frequency and allow it to emit for a set amount of time. The capacitor low side switch 522 and the inductor low side switch 524 are then closed to ring down the coil 504, which remains off for a set period until time to again ring up the coil 504. In this manner, a carrier on/off protocol can be effectively implemented to uplink data. As an alternative, the coil 504 may be allowed to ring down by closing the tank switch 520, closing switches 522 and 524 or by opening all switches and allowing the tank to ring down at its natural frequency.

During telemetry uplink where the tuning may remain at the recharge frequency, such as during a recharge period, the tuning switch 518 is maintained to tune the tank circuit 416 to the recharge frequency. The H-bridge may continue to be operated by opening the capacitor high side switch 530 and the inductor low side switch 524 while the inductor high side switch 532 and the capacitor low side switch 522 are closed. After a set amount of time defined by the telemetry frequency, the inductor high side switch 532 and the capacitor low side switch 522 are opened while the capacitor high side switch 530 and the inductor low side switch 524 are closed. These pairings continue to alternate states to ring up the coil 504 at the telemetry frequency and allow it to emit for a set amount of time. The capacitor low side switch 522 and the inductor low side switch 524 are then closed to ring down the coil 504, which remains off for a set period until time to again ring up the coil 504. In this manner, a carrier on/off protocol can be effectively implemented to uplink data. As an alternative, the coil 504 may be allowed to ring down by closing the tank switch 520, closing switches 522 and 524 or by opening all switches and allowing the tank to ring down at its natural frequency.

Figure 20:
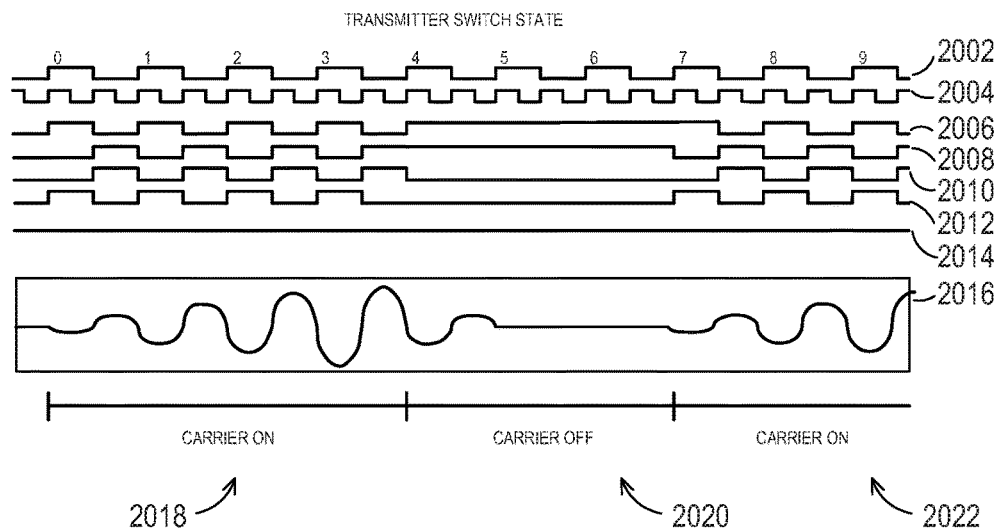
FIG. 20 shows a state of switches of one example of an IMD to establish telemetry uplink.

FIG. 20 shows a first timing chart for the H-bridge manner of telemetry uplink. The first waveform 2002 is a clock signal that is set to the telemetry frequency. The second waveform 2004 is a clock signal that is set to double the telemetry frequency but is unused in this particular method. The third and fourth waveforms 2006, 2008 correspond to the state of the capacitor low side switch 522 and the inductor low side switch 524, where a high value represents a closed state and a low value represents an open state. The fifth and sixth waveforms 2010, 2012 correspond to the state of the capacitor high side switch 530 and the inductor high side switch 532. The seventh waveform 2014 corresponds to the state of the tank switch 520 which remains open in this example.

The eighth waveform 2016 corresponds to the current through the coil 504. Sections 2018 and 2022 correspond to the ringing up and carrier on periods, while section 2020 corresponds to the carrier off period.

Figure 21:
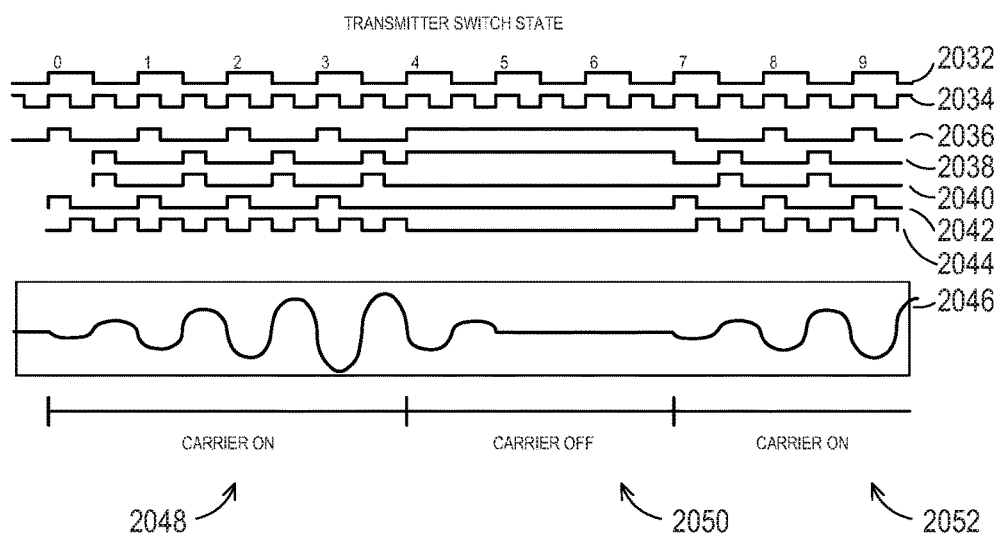
FIG. 21 shows an alternative state of switches of one example of an IMD to establish telemetry uplink.

FIG. 21 shows an alternative timing chart for the H-bridge manner of telemetry uplink where the transmission power is being throttled down by reducing the drive time of the coil 504. In this particular example, the drive time is being reduced by 50% by application of a clock frequency double that of the telemetry frequency, but other drive time reductions are applicable. Throttling down the transmission power may be done for various reasons, such as to reduce the range of the transmission for security or other purposes and/or to conserve energy. The drive time may be reduced more or less than the 50% shown in FIG. 21 for similar reasons.

The first waveform 2032 is a clock signal that is set to the telemetry frequency. The second waveform 2034 is a clock signal that is set to double the telemetry frequency. The third and fourth waveforms 2036, 2038 correspond to the state of the capacitor low side switch 522 and the inductor low side switch 524, where a high value represents a closed state and a low value represents an open state. The fifth and sixth waveforms 2040, 2042 correspond to the state of the capacitor high side switch 530 and the inductor high side switch 532. The seventh waveform 2044 corresponds to the state of the tank switch 520.

The eighth waveform 2046 corresponds to the current through the coil 504. Sections 2048 and 2052 correspond to the ringing up and carrier on periods, while section 2050 corresponds to the carrier off period.

As can be seen, the H-bridge switches are closed for half as long as in the example of FIG. 20, and the tank switch 520 is closed for the remaining half of each telemetry clock cycle portion when all the H-bridge switches are open. As a result, the current in the coil 504 rings up to a fraction of the amount of current achieved in the example of FIG. 20.

The telemetry uplink may be established in other ways as well by using switches on either side of the tank circuit 416 to ring the coil 504. For example, the capacitor low side switch 522 and the inductor high side switch 532 may be briefly closed, then opened while leaving the other switches open and then letting the tank circuit 416 ring down by closing the tank switch 520 or by closing both the capacitor low side switch 522 and the inductor low side switch 524.

Figure 6:
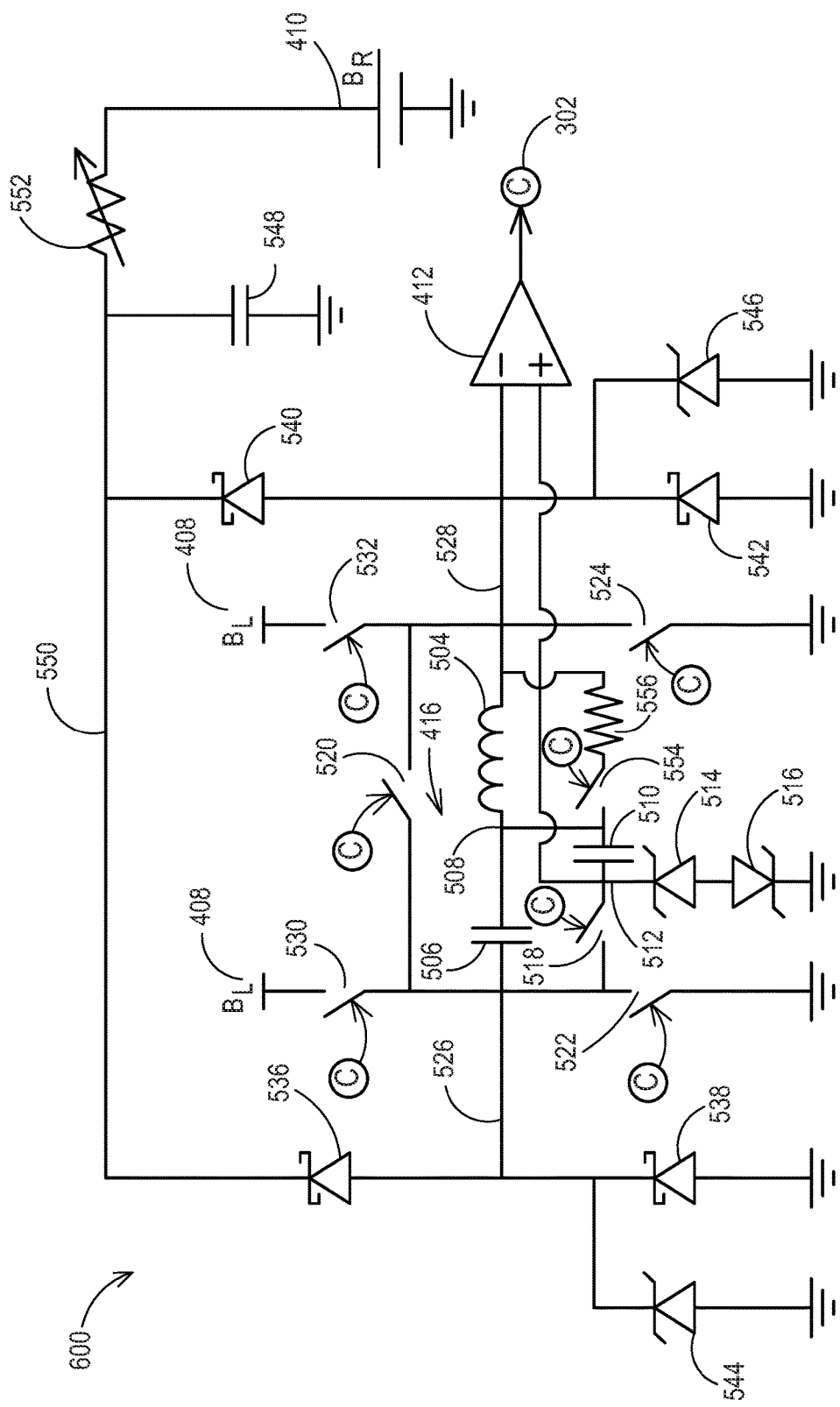
FIG. 6 shows a circuit of one example of an IMD that provides for telemetry uplink and telemetry downlink and recharge with a single coil while including a snubbing resistor for power management and/or telemetry uplink.

FIG. 6 shows a second configuration 600 which is identical to the first configuration 500 of FIG. 5 except that a circuit pathway is provided that includes a snubbing resistor 556 and a snubbing switch 554 that is under control of the processor/controller 302 in parallel with the coil 504. This circuit pathway provides power management in the event of an overcharge condition in addition to or as an alternative to the power management methods discussed above for FIG. 5. Because the snubbing switch 554 may be closed to allow some tank circuit current to pass through the snubbing resistor to dissipate the energy as heat in that component and to lower the Q of the tank circuit 416, there is less energy to be dissipated by the Zener devices 542, 544 and 514, 516.

This circuit pathway including the snubbing switch 554 and snubbing resistor 556 may have other uses as well. For instance, the telemetry of the external device 102 may be configured to receive information by monitoring for a change in the mutual inductance between the coil of the external device 102 and the coil 504 of the IMD 108 that is caused by the IMD 108 while the external device 102 is emitting a signal. This change in the mutual inductance by the IMD 108 can be viewed as a transmission of information, for example where an on-off fashion of the change in mutual inductance is similar to a carrier on-off protocol. In such a case, the H-bridge may be unnecessary and the capacitor high side switch 530 and inductor high side switch 532 may be omitted, although low side switches 522 and 524 may be retained for other purposes such as to ground the tank circuit 416.

The circuit pathway including the snubbing switch 554 and the snubbing resistor 556 is shown in the configuration 600 of FIG. 6 as a modification to the configuration 500 of FIG. 5. However, it will be appreciated that this circuit pathway may be included as a modification to other configurations as well, including those discussed below in relation to FIGS. 7-19 and 22-24.

Figure 7:
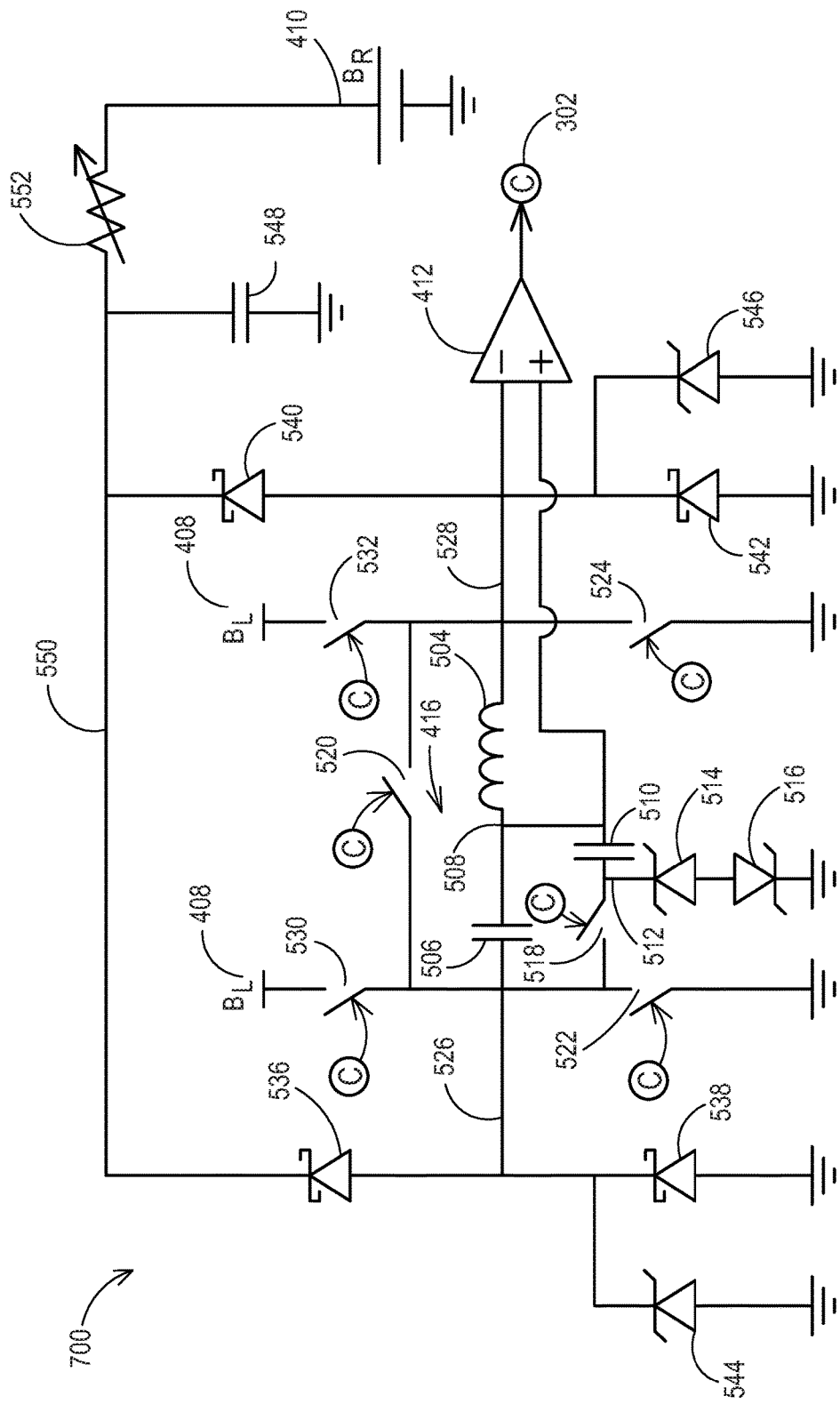
FIG. 7 shows a circuit of one example of an IMD that provides for telemetry uplink and telemetry downlink and recharge with a single coil and with a second receiver configuration.

FIG. 7 shows another configuration 700 that is the same as the configuration 500 of FIG. 5 except that the receiver's connectivity is configured differently. In this example, a receiver input is coupled directly to the high voltage node 508, rather than being capacitively coupled through the second capacitor 510.

Figure 8:
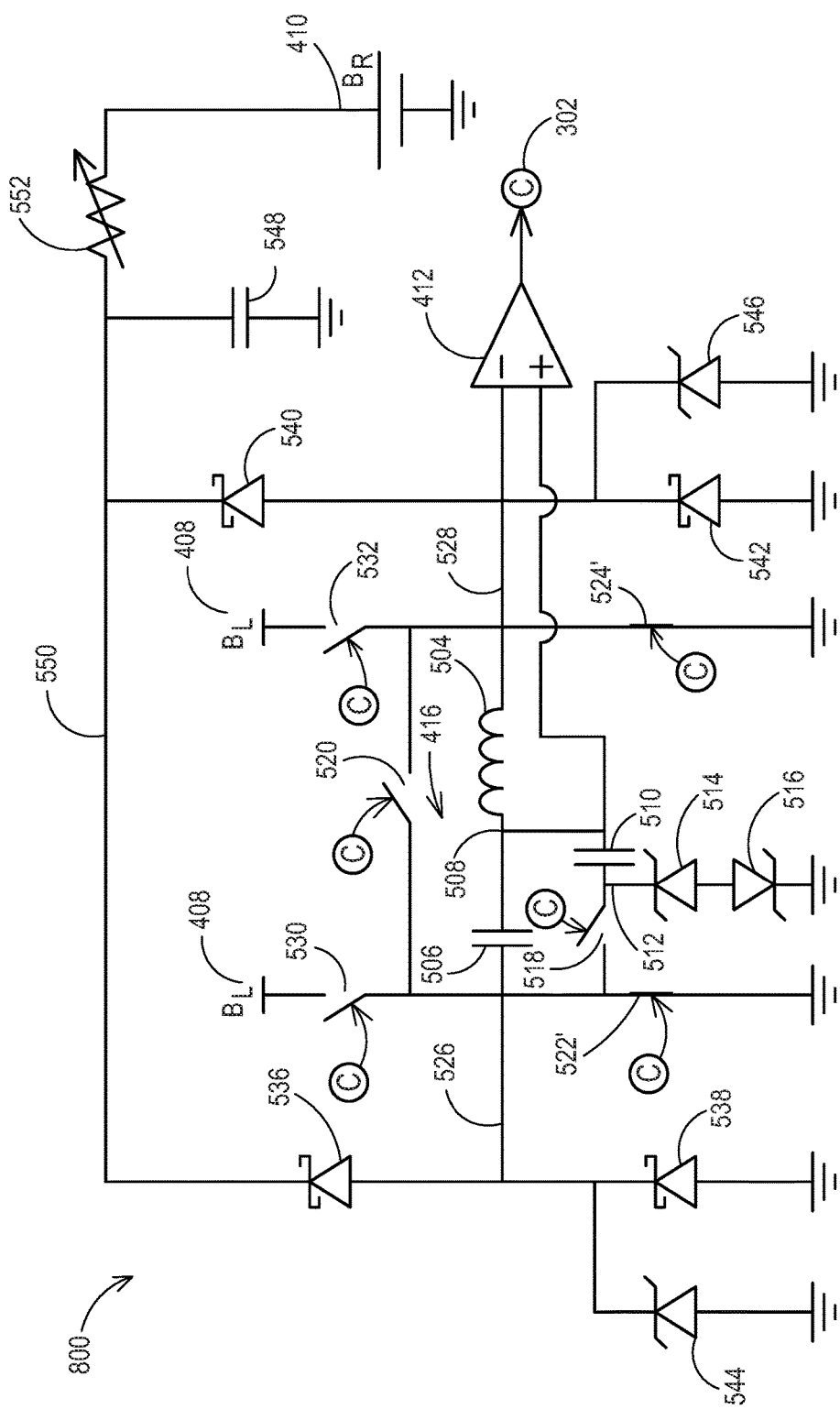
FIG. 8 shows a circuit of one example of an IMD that provides for telemetry uplink and telemetry downlink and recharge with a single coil and with a third receiver configuration.

FIG. 8 shows another configuration 800 that is the same as the configuration 700 of FIG. 7 except that the receiver's connectivity is configured differently. In this example, a receiver input is coupled directly to the high voltage node 508, rather than being capacitively coupled through the second capacitor 510, but both the capacitor side node 526 and the inductor side node 528 are connected to ground by closed switches 522' and 524' when receiving telemetry signals while all other switches are open.

Figure 9:
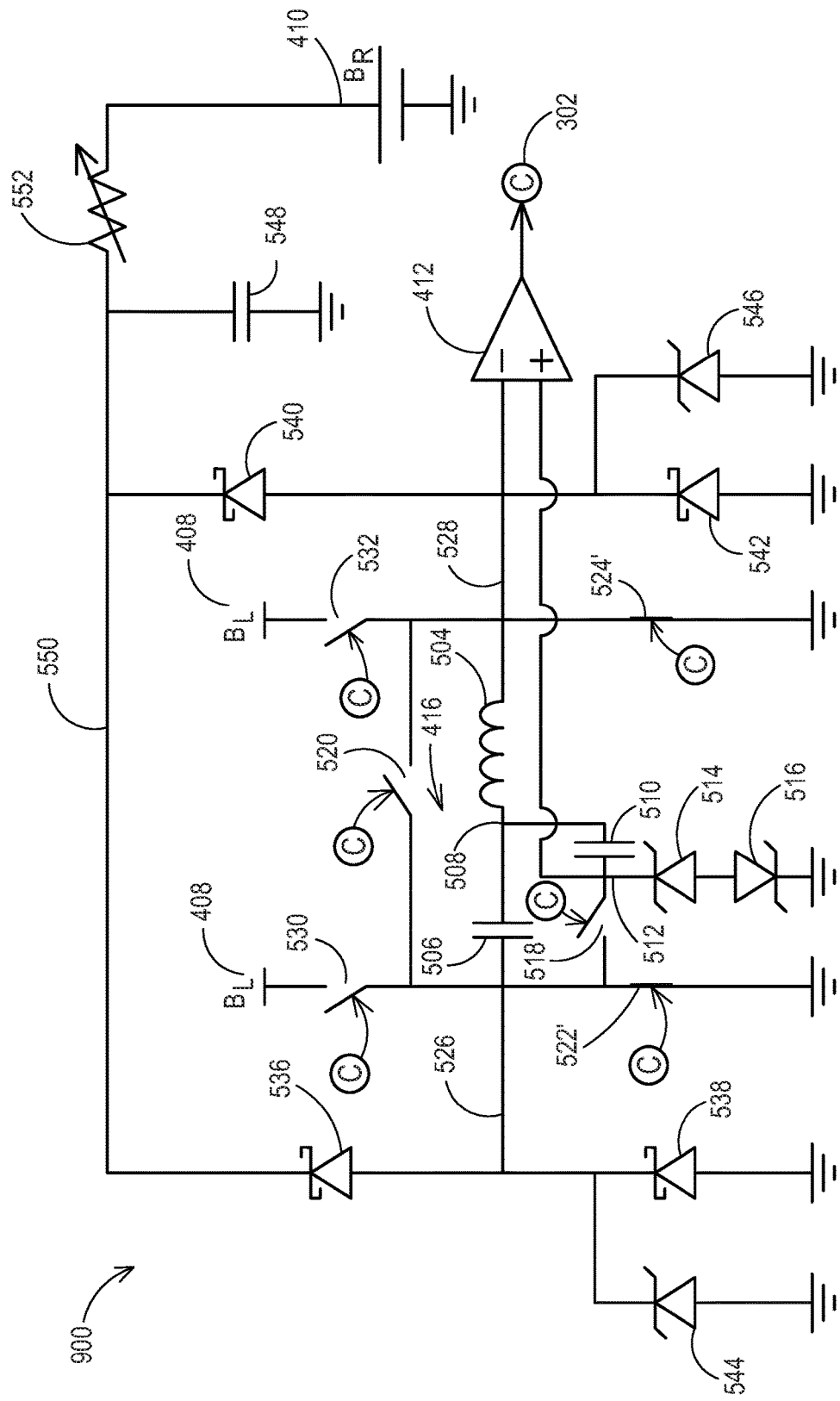
FIG. 9 shows a circuit of one example of an IMD that provides for telemetry uplink and telemetry downlink and recharge with a single coil and with a fourth receiver configuration.

FIG. 9 shows another configuration 900 that is the same as the configuration 500 of FIG. 5 except that the receiver's connectivity is configured differently. In this example, a receiver input is capacitively coupled to the high voltage node 508 through the second capacitor 510, but both the capacitor side node 526 and the inductor side node 528 are connected to ground by closed switches 522' and 524' when receiving telemetry signals while all other switches are open.

Figure 10:
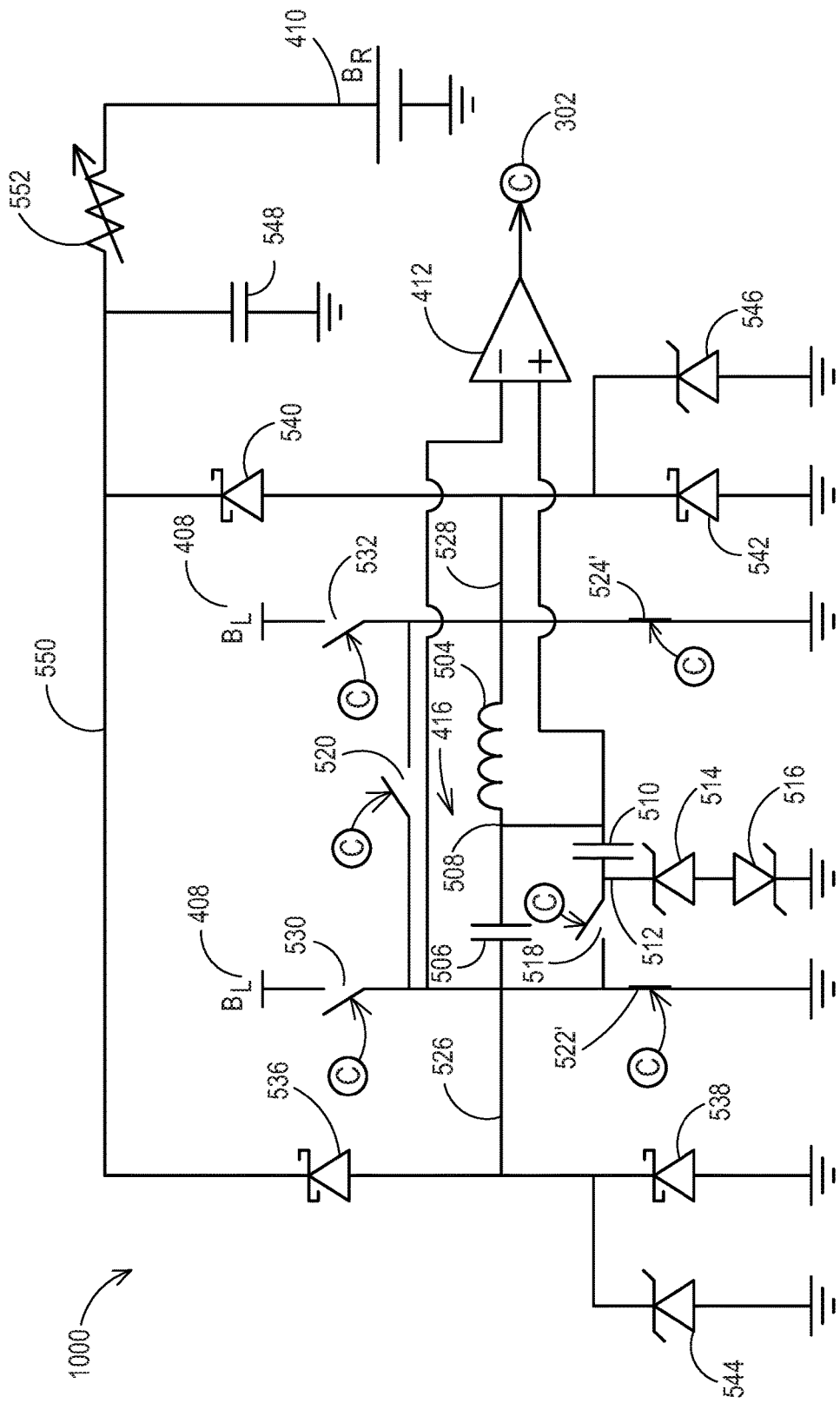
FIG. 10 shows a circuit of one example of an IMD that provides for telemetry uplink and telemetry downlink and recharge with a single coil and with a fifth receiver configuration.

FIG. 10 shows another configuration 1000 that is the same as the configuration 800 of FIG. 8 except that the receiver's connectivity is configured differently. In this example, a receiver input is coupled directly to the high voltage node 508, rather than being capacitively coupled through the second capacitor 510, and both the capacitor side node 526 and the inductor side node 528 are connected to ground by closed switches 522' and 524' when receiving telemetry signals while all other switches are open. However, the other input of the receiver 412 is connected to the capacitor side node 526 rather than the inductor side node 528.

Figure 11:
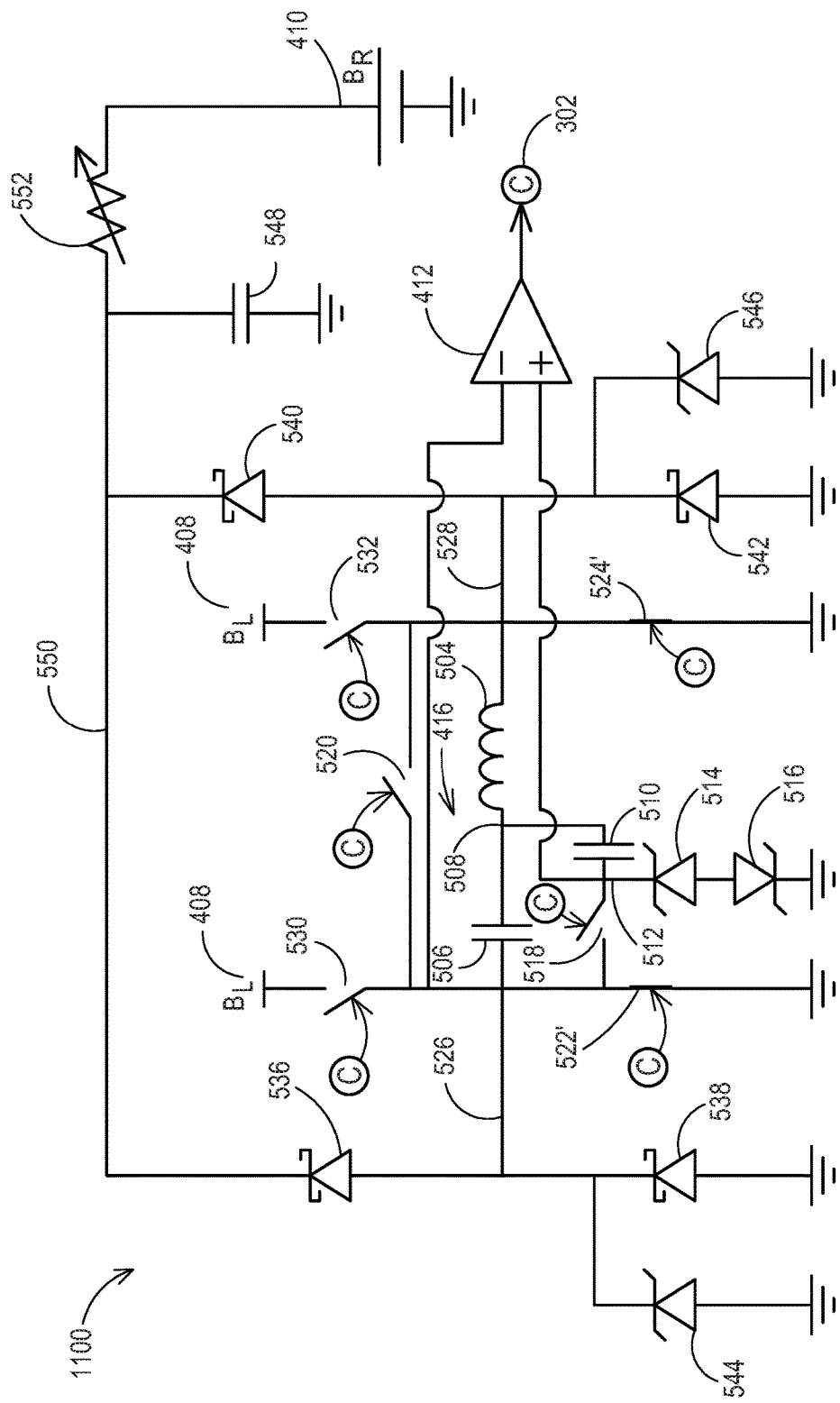
FIG. 11 shows a circuit of one example of an IMD that provides for telemetry uplink and telemetry downlink and recharge with a single coil and with a sixth receiver configuration.

FIG. 11 shows another configuration 1100 that is the same as the configuration 900 of FIG. 9 except that the receiver's connectivity is configured differently. In this example, a receiver input is capacitively coupled to the high voltage node 508 through the second capacitor 510, and both the capacitor side node 526 and the inductor side node 528 are connected to ground by closed switches 522' and 524' when receiving telemetry signals while all other switches are open. However, the other input of the receiver 412 is connected to the capacitor side node 526 rather than the inductor side node 528.

Figure 12:
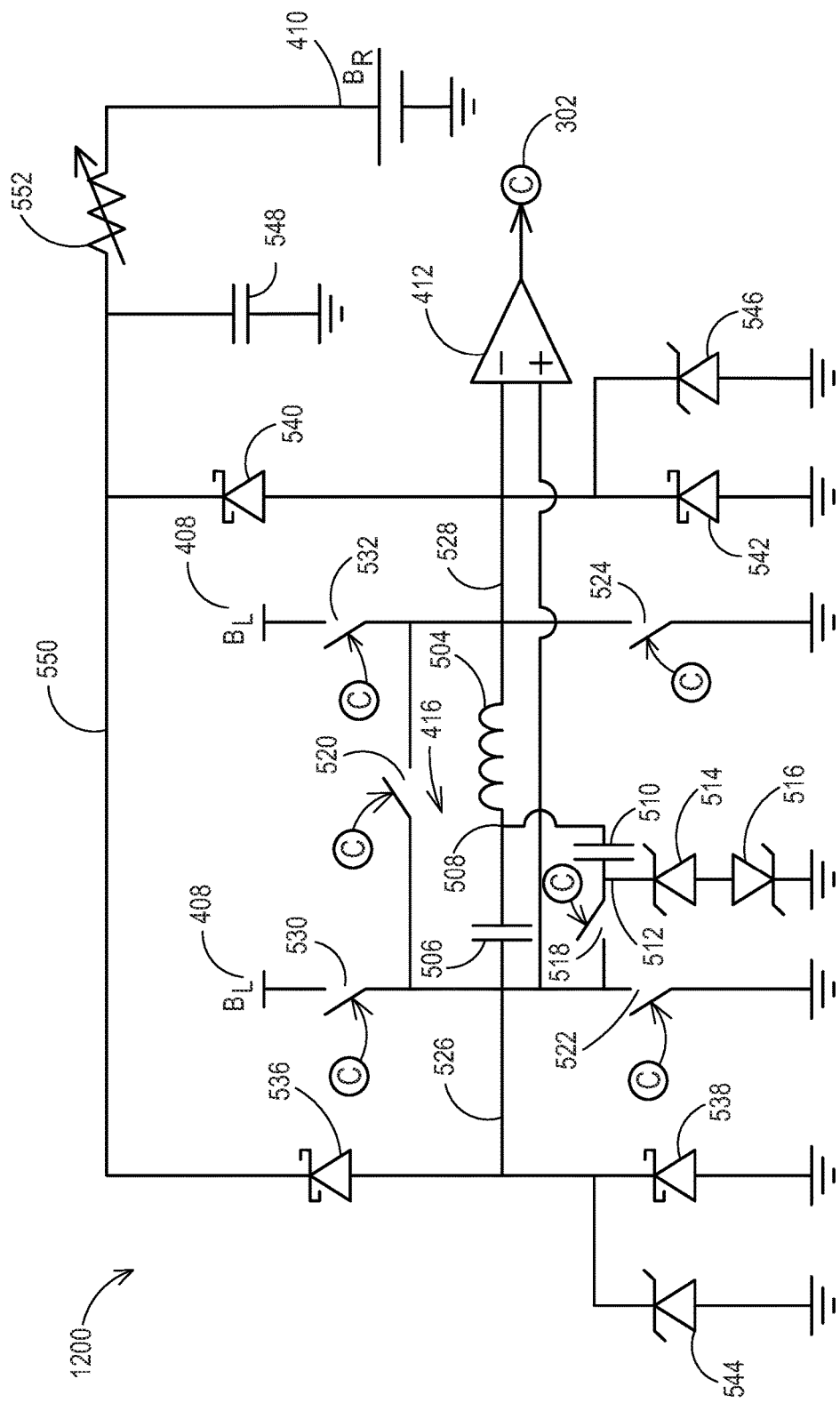
FIG. 12 shows a circuit of one example of an IMD that provides for telemetry uplink and telemetry downlink and recharge with a single coil and with a seventh receiver configuration.

FIG. 12 shows another configuration 1200 that is the same as the configuration 500 of FIG. 5 except that the receiver's connectivity is configured differently. Here, the receiver is connected differentially across the tank circuit 416 by having a receiver input coupled directly to the inductor side node 528 while another receiver input is coupled directly to the capacitor side node 526. All other switches are open when receiving telemetry signals.

Figure 13:
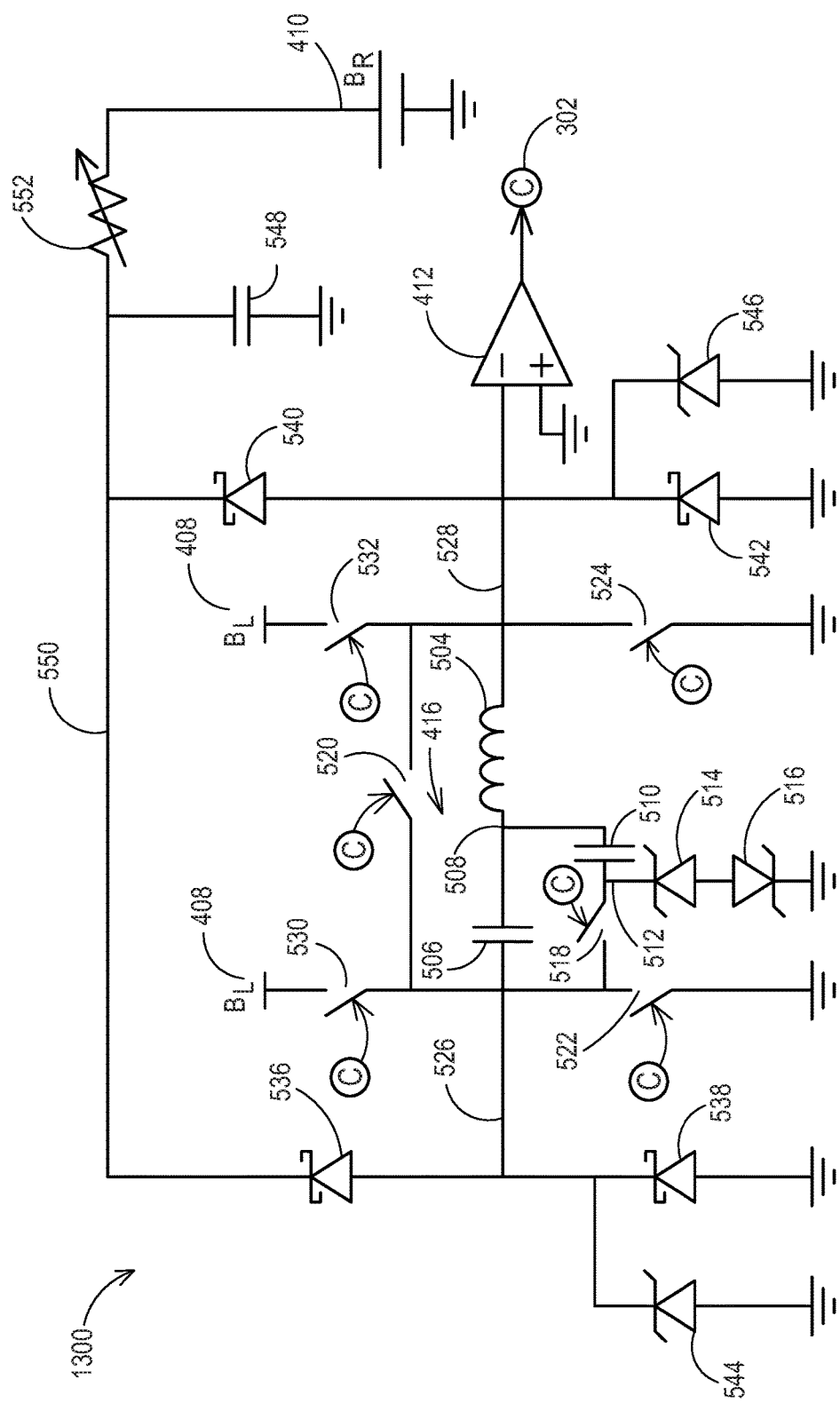
FIG. 13 shows a circuit of one example of an IMD that provides for telemetry uplink and telemetry downlink and recharge with a single coil and with an eighth receiver configuration.

FIG. 13 shows another configuration 1300 that is the same as the configuration 500 of FIG. 5 except that the receiver's connectivity is configured differently. Here, one input of the receiver 412 remains connected to the inductor side node 528 while the other input of the receiver 412 is connected to ground. All other switches are open when receiving telemetry signals or switch 520 may be closed.

Figure 14:
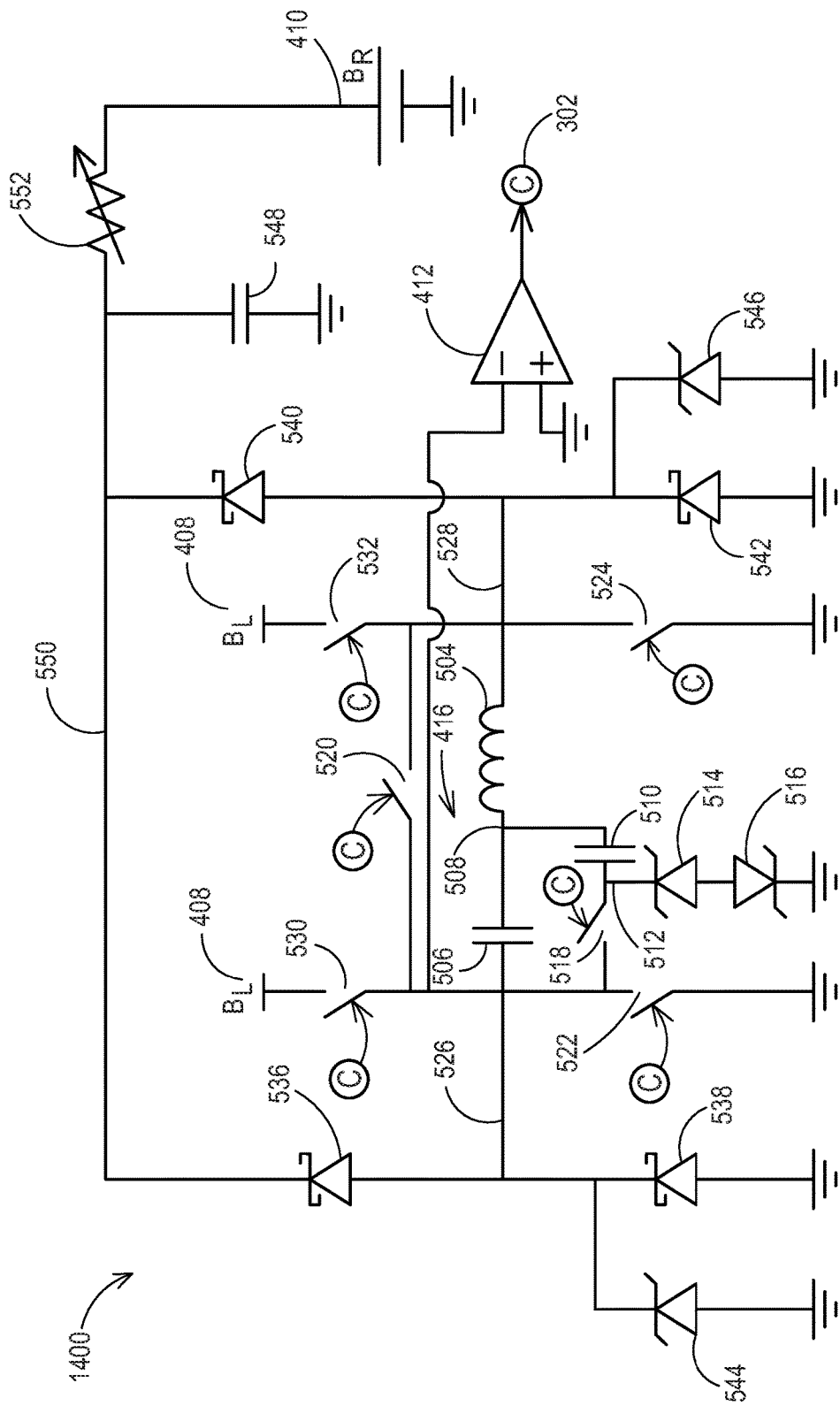
FIG. 14 shows a circuit of one example of an IMD that provides for telemetry uplink and telemetry downlink and recharge with a single coil and with a ninth receiver configuration.

FIG. 14 shows another configuration 1400 that is the same as the configuration 500 of FIG. 5 except that the receiver's connectivity is configured differently. Here, one input of the receiver 412 is connected to the capacitor side node 526 while the other input of the receiver 412 is connected to ground. All other switches are open when receiving telemetry signals or switch 520 may be closed.

Figure 15:
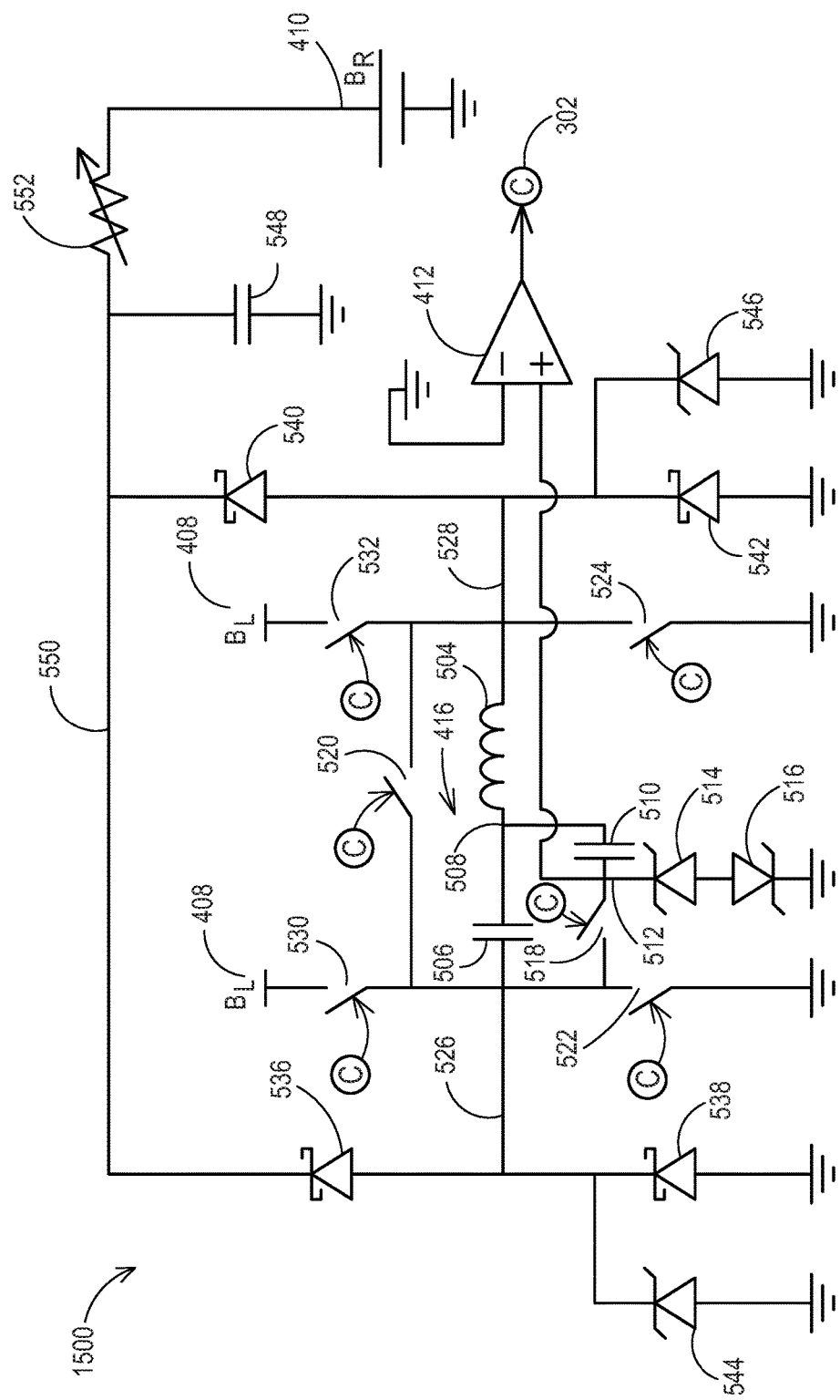
FIG. 15 shows a circuit of one example of an IMD that provides for telemetry uplink and telemetry downlink and recharge with a single coil and with a tenth receiver configuration.

FIG. 15 shows another configuration 1500 that is the same as the configuration 500 of FIG. 5 except that the receiver's connectivity is configured differently. Here, one input of the receiver 412 is connected to the additional capacitor side node 512 so as to be capacitively coupled to the high voltage node 508 while the other input of the receiver 412 is connected to ground. All other switches are open when receiving telemetry signals or switch 520 may be closed.

Figure 16:
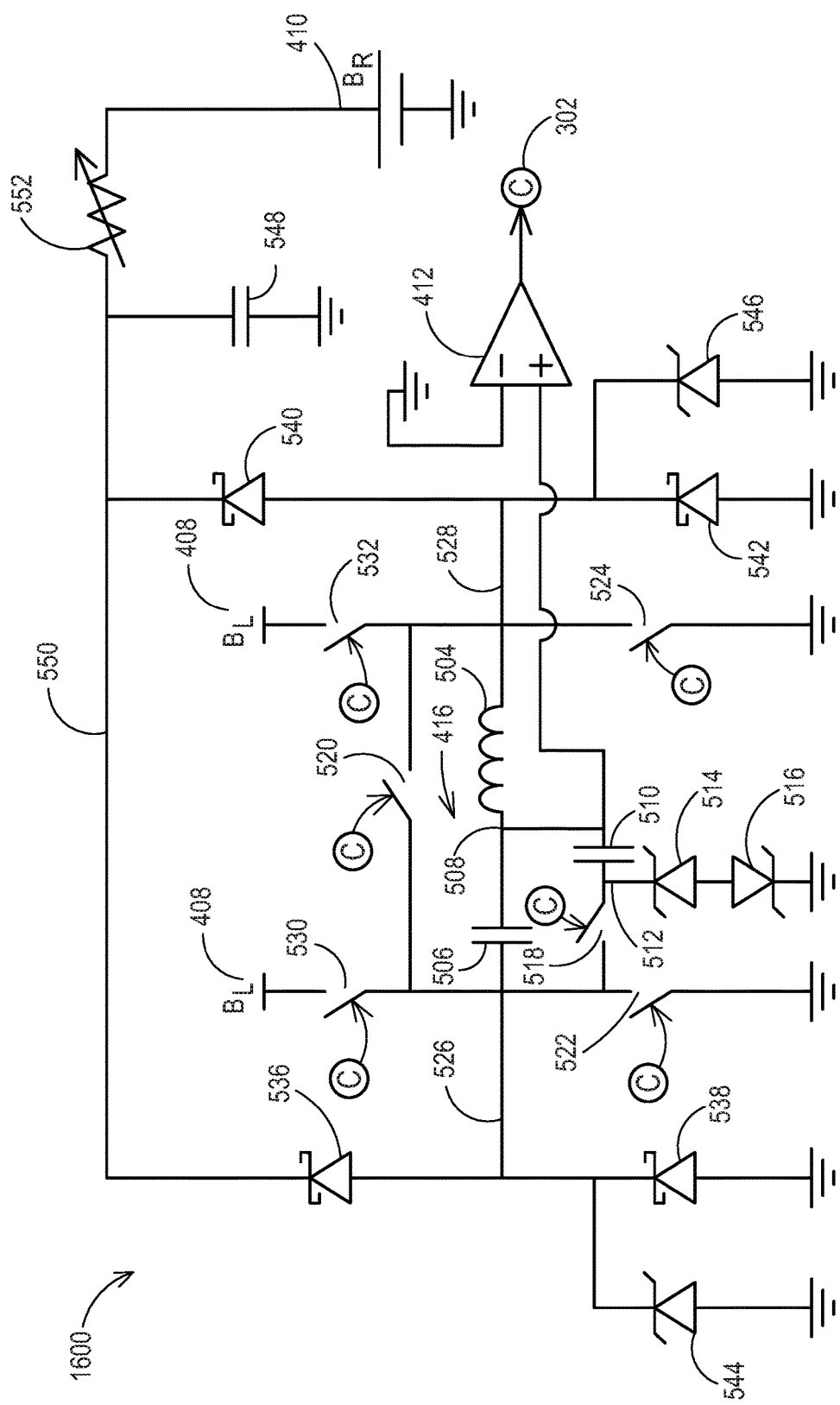
FIG. 16 shows a circuit of one example of an IMD that provides for telemetry uplink and telemetry downlink and recharge with a single coil and with an eleventh receiver configuration.

FIG. 16 shows another configuration 1600 that is the same as the configuration 500 of FIG. 5 except that the receiver's connectivity is configured differently. Here, one input of the receiver 412 is connected directly to the high voltage node 508 while the other input of the receiver 412 is connected to ground. All other switches are open when receiving telemetry signals or switch 520 may be closed.

Figure 17:
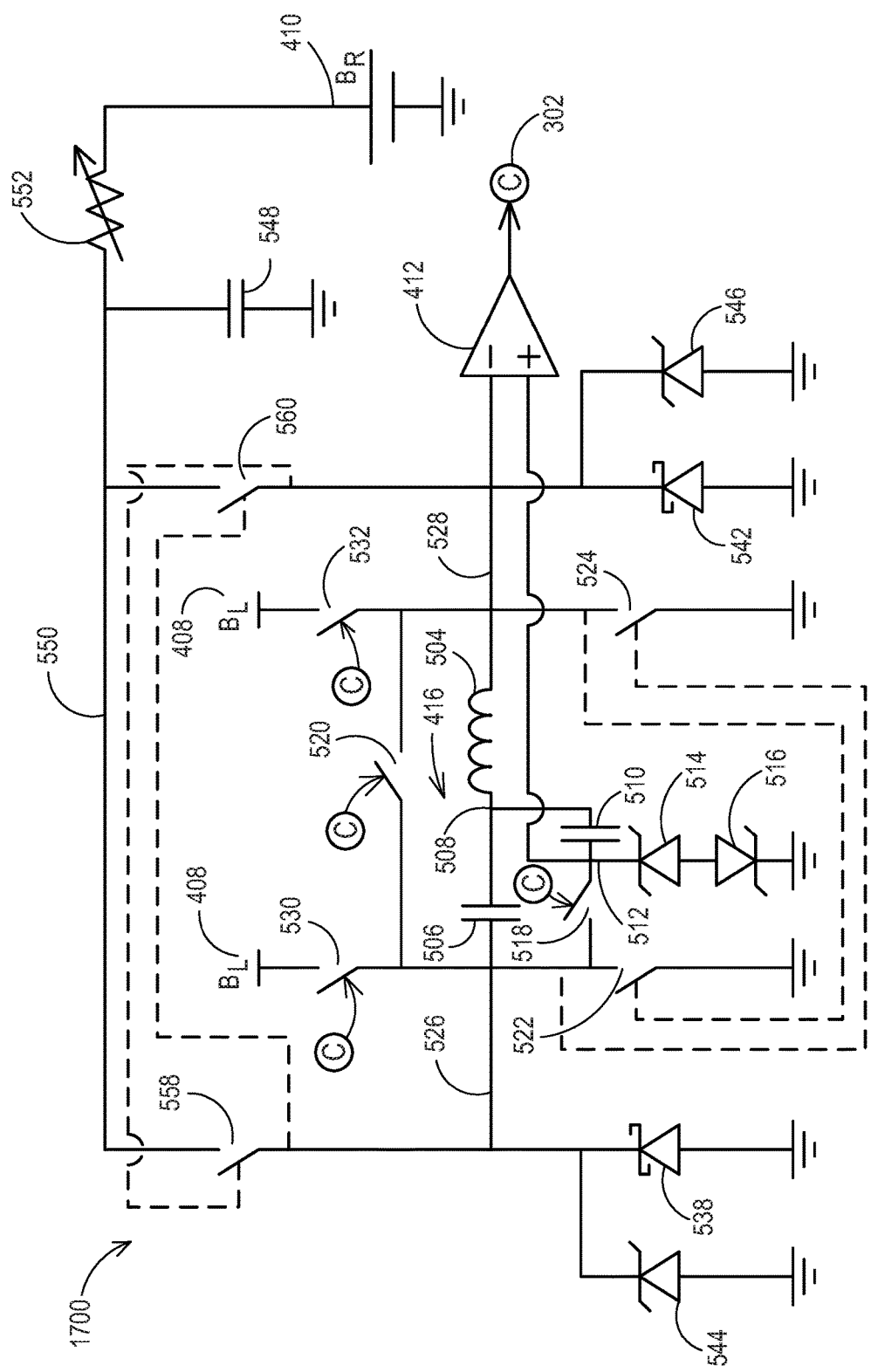
FIG. 17 shows a circuit of one example of an IMD that provides for telemetry uplink and telemetry downlink and recharge with a single coil and with a second rectifier configuration.

FIG. 17 shows a configuration 1700 that is the same as the configuration 500 of FIG. 5 except that the rectifier is different. In this configuration 1700, the rectifier may use both high side and low side synchronous rectification by including a capacitor high side rectifier switch 558 and an inductor high side rectifier switch 560 in place of high side diodes. As discussed for the configuration of FIG. 5, the capacitor low side switch 522 and the inductor low side switch 524 may operate to provide the low side synchronous rectification.

In this particular example, the low side synchronous rectifier switches 522, 524 may be N-MOS devices while the high side synchronous rectifier switches 558, 560 may be P-MOS devices. The result based on the state machine control by the processor/controller 302 is that when the inductor side flies high, the inductor high side switch 560 and the capacitor low side switch 522 are closed while the capacitor high side switch 558 and the inductor low side switch 524 are open. When the capacitor side flies high, the capacitor high side switch 558 and the inductor low side switch 524 are closed while the inductor high side switch 560 and the capacitor low side switch are open.

The synchronous rectifier of FIG. 17 may be a pure full wave synchronous rectifier as another alternative. In that case, the diodes 538 and 542 are omitted.

While this operation of the switches 522, 524, 558, and 560 applies to recharge, during uplink and downlink telemetry operations, the capacitor low side switch 522 and the inductor low side switch 524 may operate in the same manner as discussed above in relation to FIG. 5. The capacitor high side switch 558 and the inductor high side switch 560 may remain open during uplink and downlink telemetry operations.

Figure 18:
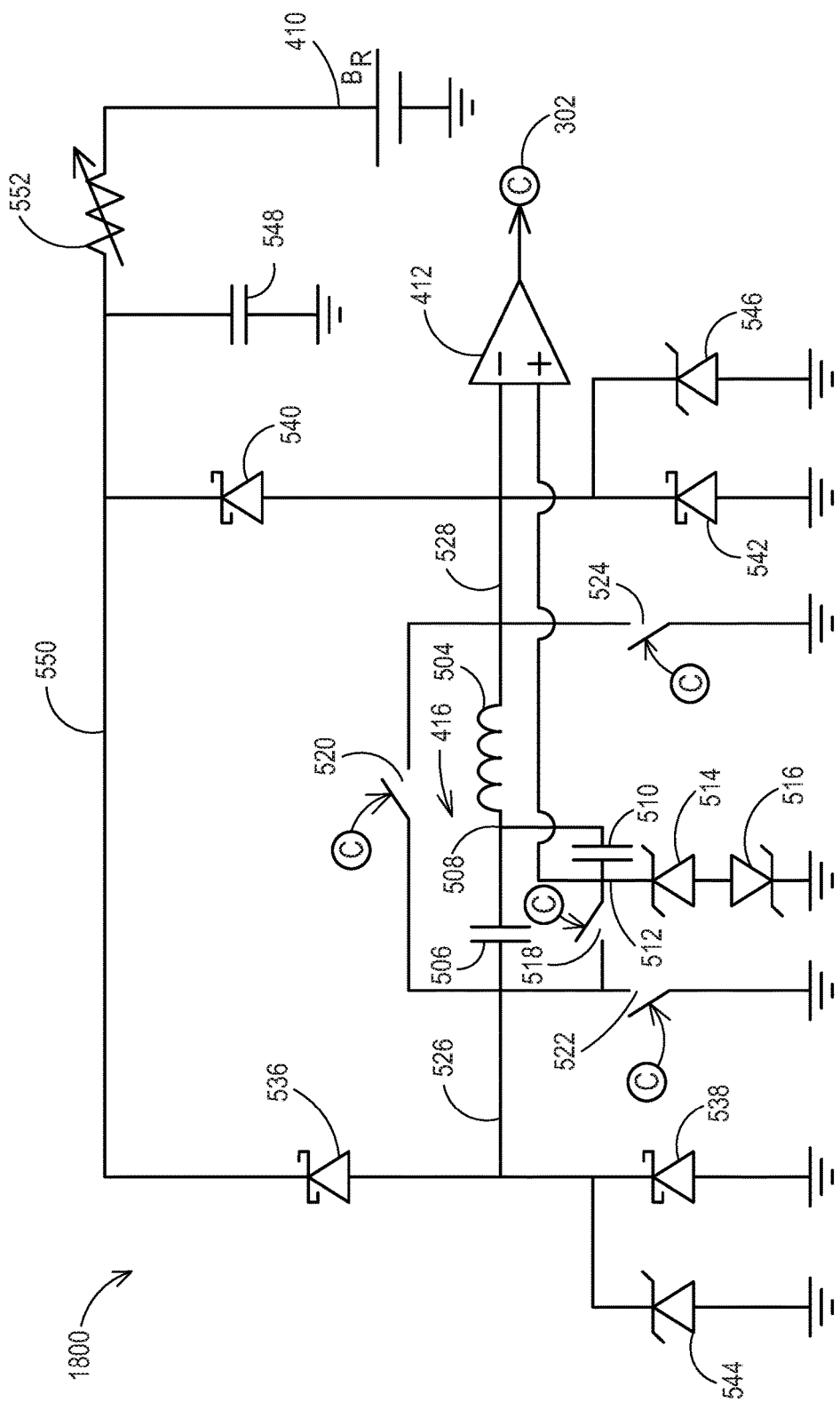
FIG. 18 shows a circuit of one example of an IMD that provides for telemetry uplink and recharge with a single coil.
Figure 23:
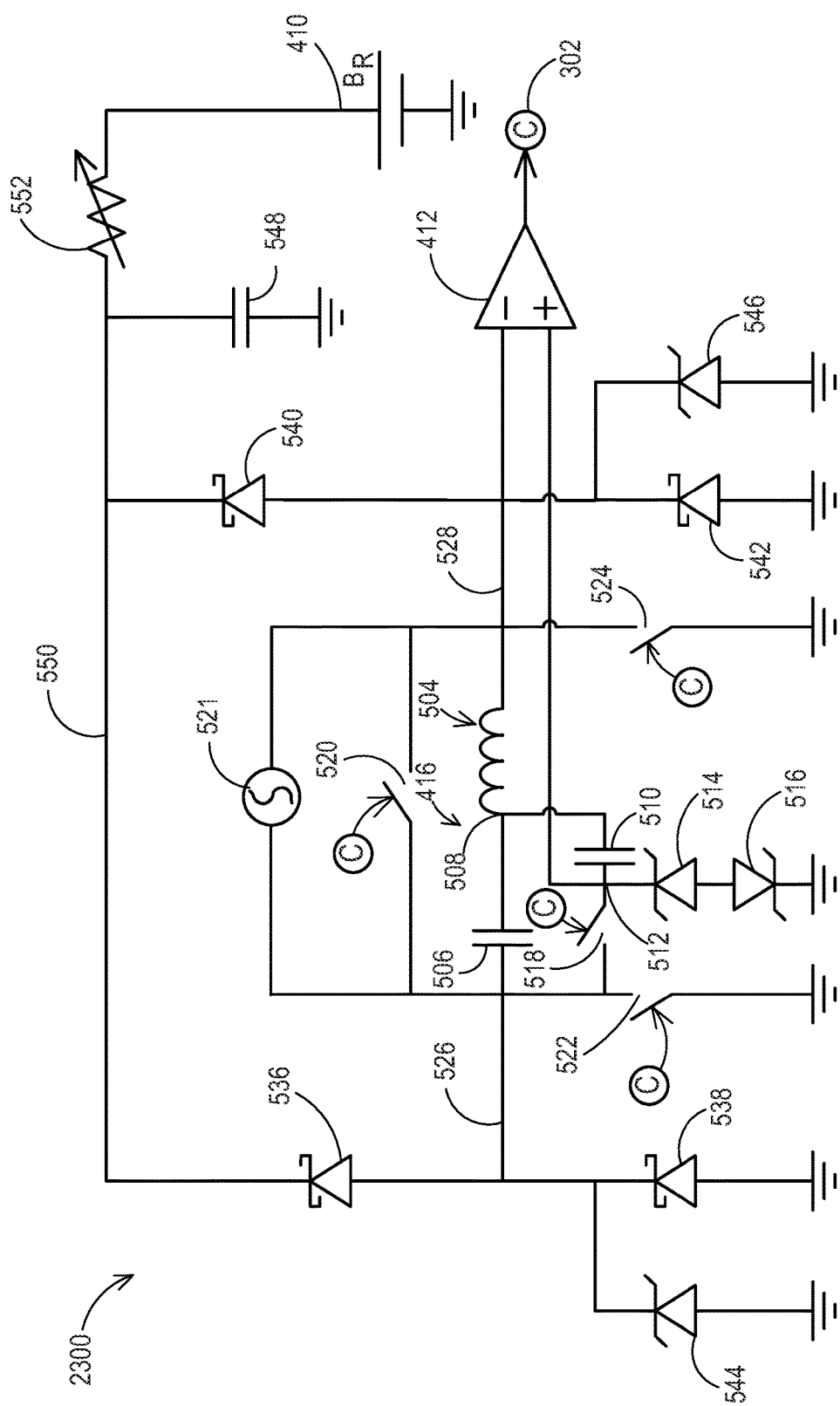
FIG. 23 shows a circuit of one example of an IMD that provides for telemetry uplink and telemetry downlink and recharge with a single coil and with a second uplink configuration and a first rectifier configuration.
Figure 24:
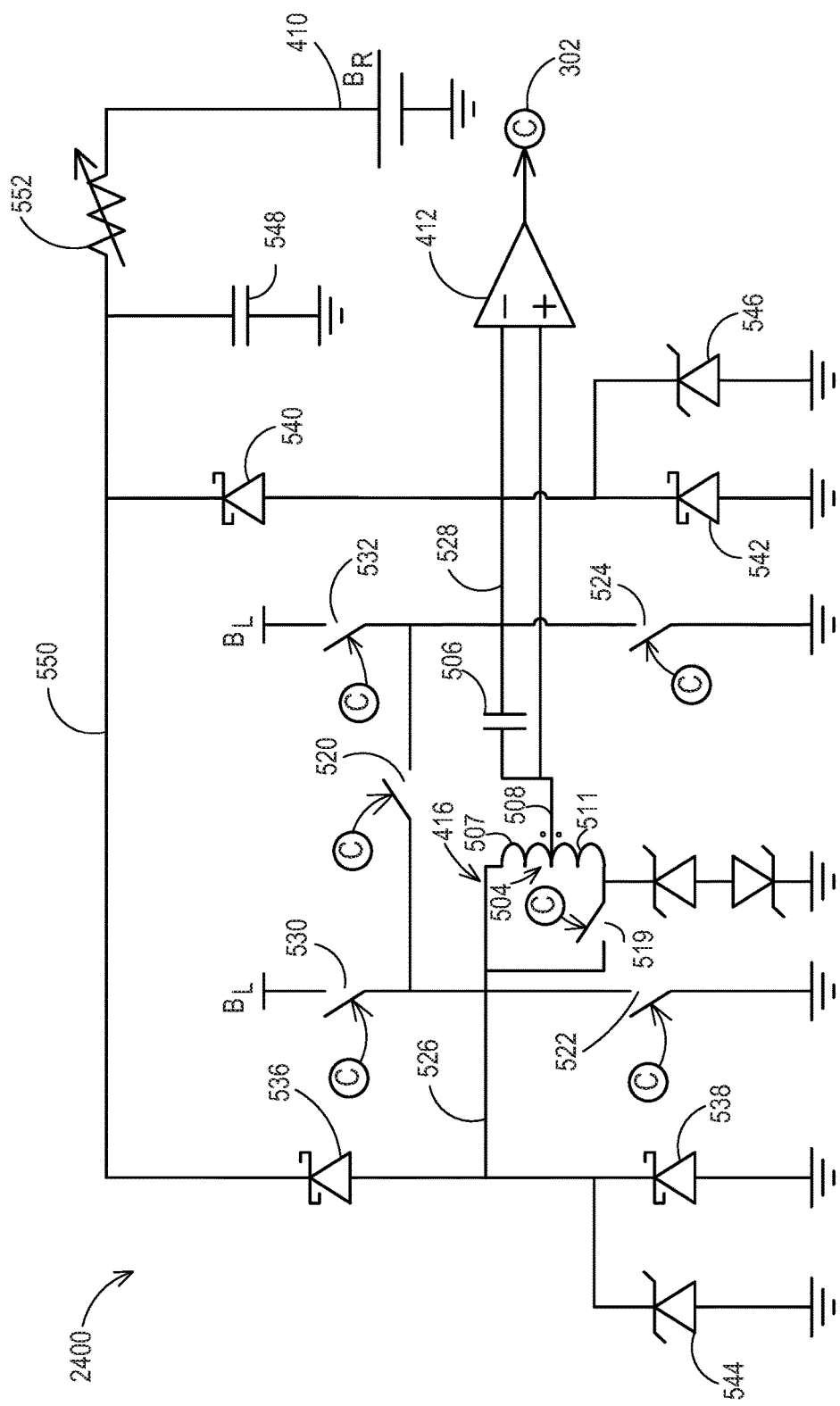
FIG. 24 shows a circuit of one example of an IMD that provides for telemetry uplink and telemetry downlink and recharge with a single capacitor and a single coil providing variable inductance and with a first receiver configuration and a first rectifier configuration.

FIG. 18 shows another configuration 1800 like the configuration 500 of FIG. 5, except that the high side of the H-bridge created by the capacitor high side switch 530 and inductor high side switch 532 has been omitted. In this situation, the coil 504 is being used for recharge and downlink telemetry. Uplink telemetry may be unnecessary in some contexts for an IMD 108. As another example, uplink telemetry may be provided at a separate frequency than downlink telemetry and may utilize a separate circuit and coil from that shown so that full-duplex communication with the external device 102 may be achieved. The variations discussed above in FIGS. 5-17 and below in FIGS. 22-24 are also applicable to the configuration 1800 to the extent those variations relate to recharging, telemetry downlink, and power management.

Figure 19:
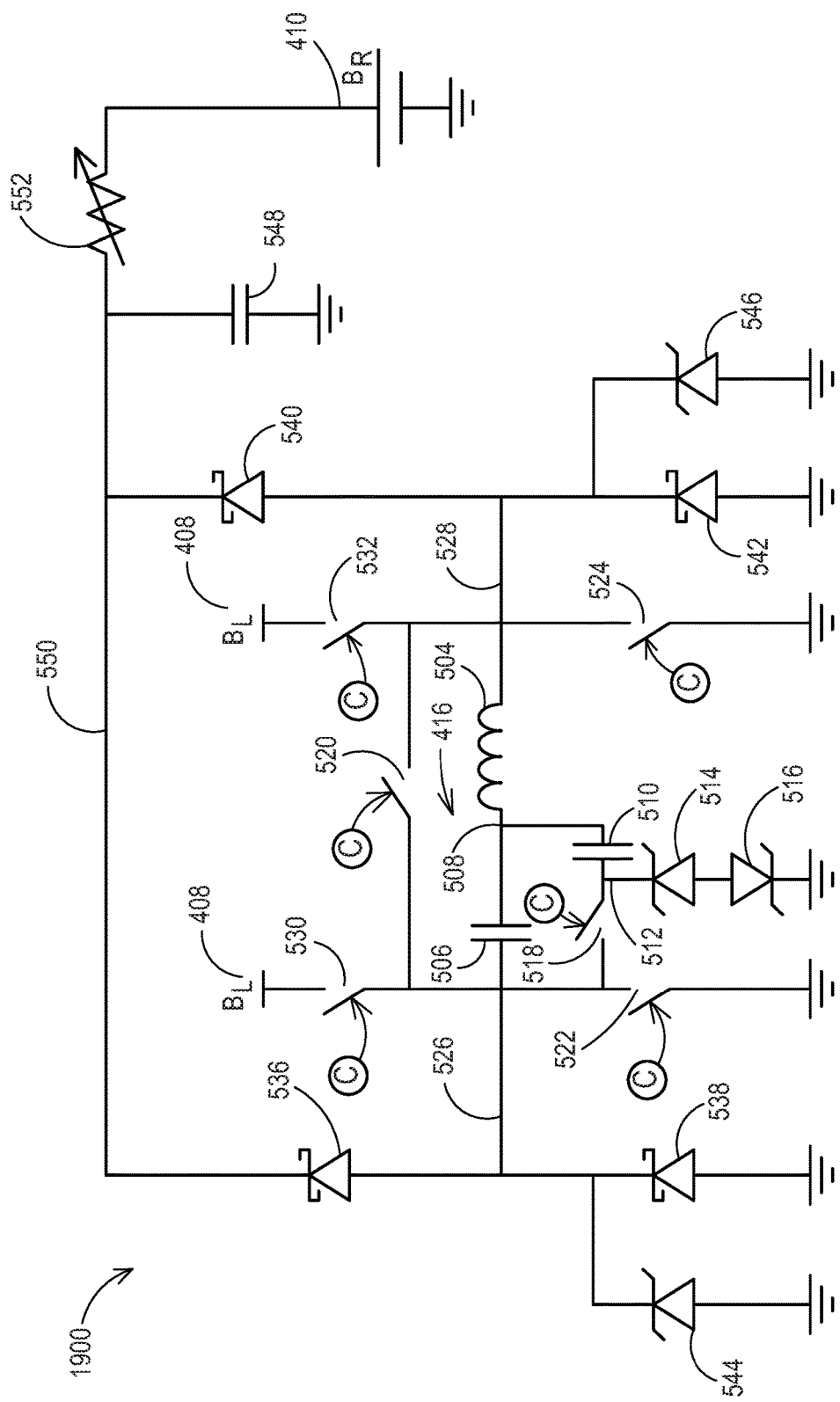
FIG. 19 shows a circuit of one example of an IMD that provides for telemetry downlink and recharge with a single coil.

FIG. 19 shows another configuration 1900 like the configuration 500 of FIG. 5, except that the receiver 412 has been omitted. In this situation, the coil 504 is being used for recharge and uplink telemetry. Downlink telemetry may be unnecessary in some contexts for an IMD 108. As another example, downlink telemetry may be provided at a separate frequency than uplink telemetry and may utilize a separate circuit and coil from that shown so that full-duplex communication with the external device 102 may be achieved. The variations discussed above in FIGS. 5, 6, and 17 and below in relation to FIGS. 22-24 are also applicable to the configuration 1900 to the extent those variations relate to recharging, telemetry uplink, and power management.

Figure 22:
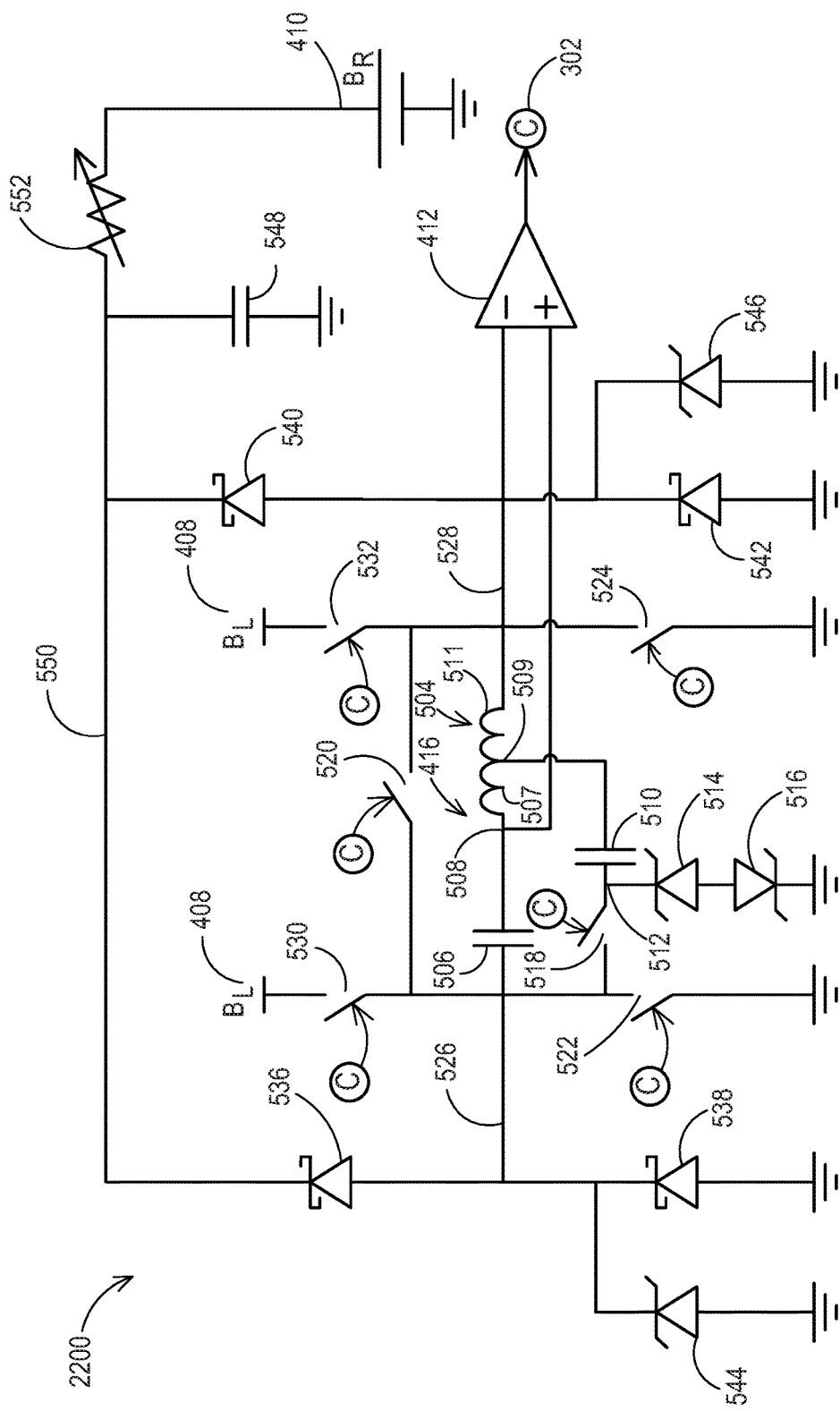
FIG. 22 shows a circuit of one example of an IMD that provides for telemetry uplink and telemetry downlink and recharge with a single coil having a tap that provides a voltage divider and with a first receiver configuration and a first rectifier configuration.

FIG. 22 shows another configuration 2200 like the configuration 500 of FIG. 5 except that the second capacitor 510 does not connect to the high voltage node 508 while the receiver 534 is DC coupled to the high voltage node 508. In this example, the coil 504 is provided with a tap creating an intermediate node 509 and creating a first coil portion 507 and a second coil portion 509. The second capacitor 510 connects to the tap in the coil providing the intermediate node 509. A voltage divider effect is provided whereby the voltage at the intermediate node 509 which AC couples to the node 512 and tuning switch 518 is less than the voltage on the high voltage node 508. This provides additional protection to the tuning switch 518.

It will be appreciated that the selection of the capacitance for the second capacitor 510 will be different than the selection of the capacitance for the second capacitor 510 in the configuration 500 of FIG. 5 in order to tune to the same recharge frequency. It will also be appreciated that all of the variations discussed above in FIGS. 5-19 are also applicable to the example of FIG. 22, including coupling the receiver 412 to nodes besides the high voltage node 508.

FIG. 23 shows another configuration 2300 like the configuration 500 of FIG. 5 except that the transmission switches 522, 524, 530, and 532 are no longer being used to ring the coil 504. Instead, an oscillator 521 such as a sinusoidal power amplifier is connected across the tank circuit 416 to drive the tank circuit at the uplink frequency. The oscillator 521 may be activated and deactivated by the controller 302 which may also switch the oscillator 521 into and out of the circuit. The capacitor high side switch 530 and the inductor high side switch 532 may be omitted as shown. This oscillator 521 may result in fewer harmonics on the uplink carrier. It will be appreciated that all of the variations discussed above in FIGS. 5-19 and 22 are also applicable to the example of FIG. 23.

FIG. 24 shows another configuration 2400 like the configuration 500 of FIG. 5 except that the variable reactance is provided by varying the inductance rather than the capacitance. The variable inductance is achieved in this example with the single coil 504 by providing a tap on the coil 504 that establishes a first coil portion 507 and a second coil portion 509. The first coil portion is connected between the node 526 and the high voltage node 508 while the second coil portion is connected between a tuning switch 519 and the high voltage node 508. The tuning switch 519 is further connected to the node 526. A first capacitor 506 is connected between the high voltage node 508 and the node 528.

As can be seen by the dot convention of the coil 504, the first coil portion 507 and the second coil portion 509 are geometrically oriented so that their currents are directed in phase to the high voltage node 508. This may be accomplished by changing the direction of the turns of the coil of the second coil portion 509 relative to the first coil portion 507, such as where a bobbin carrying both coil portions 507, 509 is linear. As another example, this may be accomplished by maintaining the direction of the turns about the bobbin but by reversing the direction of the bobbin at the tap such as by having a U-shape.

The controller 302 operates the tuning switch 519 to switch the second coil portion 509 into and out of the tank 416. In doing so, the controller 302 is tuning the tank 416 either to the telemetry frequency or to the recharge frequency. It will be appreciated that all of the variations discussed above in FIGS. 5-19, 22 and 23 are also applicable to the example of FIG. 24.

Figure 25:
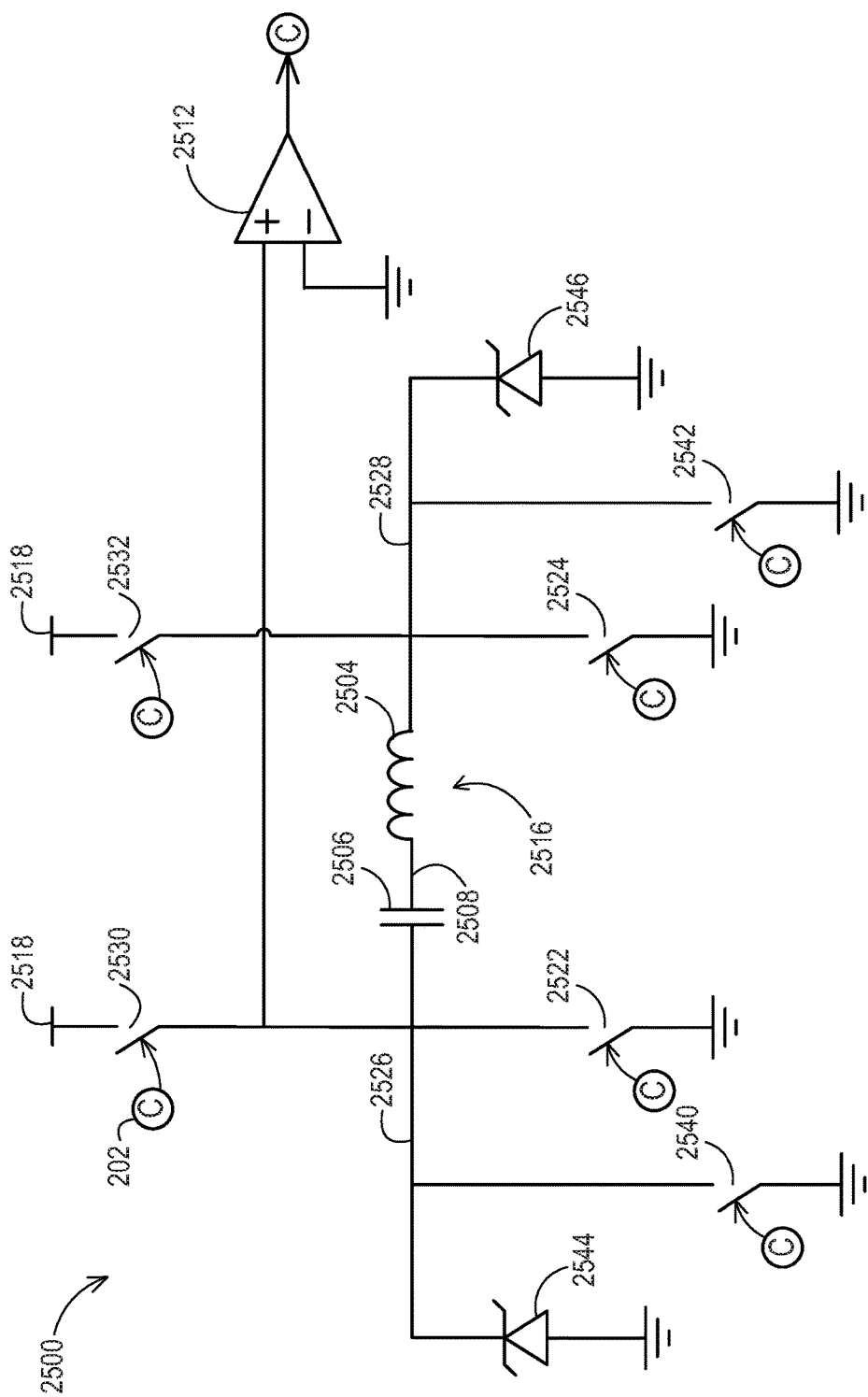
FIG. 25 shows a circuit of one example of an external recharge device that provides for telemetry uplink and telemetry downlink and recharge with a single coil and with a first receiver configuration.

FIG. 25 shows a first configuration 2500 for a circuit of the external recharge device 102' that provides for telemetry uplink and downlink at a telemetry frequency during a recharge period with a tank circuit tuned to the recharge frequency. Like the configurations of the IMD 108, the first configuration 2500 includes switches implemented in silicon.

The first configuration includes the tank circuit 2516 that has a coil 2504 and a fixed reactance that is provided by a fixed capacitance. The fixed capacitance is achieved in this example by providing a first capacitor 2506 that is hardwired in series with the coil 2504.

The tank circuit 2516 establishes several nodes. An inductor side node 2528, a capacitor side node 2526, and a high voltage node 2508 are achieved. The high voltage node 2508 acquires a relatively high voltage periodically as the voltage swings within the tank circuit 2516. Capacitor low side switches 2522, 2540 and inductor low side switches 2524, 2542 along with capacitor high side switch 2530 and inductor high side switch 2532 are also present and are discussed below. The switches 2522, 2524, 2530, and 2532 form an H-bridge that can be used for telemetry downlink to the IMD 108 as well as to emit recharge energy to the IMD 108 where the switches 2530 and 2532 are connected to a voltage source 2518 from the battery. The switches 2522 and 2524 provide a strong ground, i.e., low impedance to ground, for recharge and telemetry transmission purposes while the switches 2540 and 2542 provide a weak ground, i.e., higher impedance to ground, for telemetry reception purposes.

A capacitor side Zener diode 2544 and an inductor side Zener diode 2546 are also present. These devices limit voltage swings on the capacitor side node 2526 and the inductor side node 2528 to prevent over-voltage damage from occurring on voltage sensitive devices connected to these nodes. Voltage sensitive devices may include the various switches which are implemented in silicon and particularly those that are implemented as monolithic devices. As can be seen, no voltage sensitive device is coupled to the high voltage node 2508 which reduces the likelihood of any damage to those voltage sensitive devices.

This embodiment of the external recharge device 102' is capable of directing recharge energy to the IMD 108 by using the tank circuit 2516 and one of various driver circuits and related methods, such as the H-bridge or an oscillator. For instance, as shown, the H-bridge may be used to transmit recharge energy by operating the H-bridge at the recharge frequency while the tank circuit 2516 is tuned to the recharge frequency.

This embodiment of the external recharge device 102' is capable of telemetry uplink from the IMD 108 by using the tank circuit 2516. The receiver 2512 is present to receive the telemetry signals induced on the coil 2504. The receiver 2512 is connected to the tank circuit 2516 in a first configuration as shown. Other configurations are also available such as those similar to the configurations for the receiver of the IMD 108 in FIGS. 6-19 and 22-24. In this example, a first input of the receiver 2512 is connected to the capacitor side node 2526 while another input is grounded. As the input impedance of the receiver 2512 is very high, the receiver 2512 does not appreciably affect the tuning of the tank circuit 2516. Low side switches 2540 and 2542 are present to weakly couple the tank circuit 2516 to ground when receiving telemetry.

This embodiment of the external recharge device 102' is also capable of telemetry downlink to the IMD 108 by using the tank circuit 2516 and one of various driver circuits and related methods. For instance, as shown, the H-bridge may be used to transmit telemetry signals by operating the H-bridge at the telemetry frequency even though the tank circuit 2516 remains tuned to the recharge frequency.

The various modes of operation of the configuration 2500 operate as follows. During recharge mode, the processor/controller 202 of this example operates the H-bridge or other driver circuit at the recharge frequency to drive the tank circuit 2516 to emit recharge energy at the recharge frequency by opening the capacitor high side switch 2530 and the inductor low side switch 2524 while the inductor high side switch 2532 and the capacitor low side switch 2522 are closed. Switches 2450 and 2542 remain open during recharge mode. After a set amount of time defined by the recharge frequency, the inductor high side switch 2532 and the capacitor low side switch 2522 are opened while the capacitor high side switch 2530 and the inductor low side switch 2524 are closed. These pairings continue to alternate states to ring up the coil 2504 at the recharge frequency and allow it to emit for a set amount of time. The capacitor low side switch 2522 and the inductor low side switch 2524 are then closed to ring down the coil 2504, which remains off for a set period until time to again ring up the coil 2504. As an alternative, the coil 2504 may be allowed to ring down by closing a tank switch that may be included but is not shown in this example, by closing switches 2522 and 2524 or by opening all switches and allowing the tank to ring down at its natural frequency.

During telemetry uplink occurring in the recharge period, the processor/controller 202 of this example leaves all switches open except capacitor low side switch 2540 and inductor low side switch 2542 are closed to weakly ground the capacitor side node 2526 and the inductor side node 2528, thereby grounding both sides of the tank circuit 2516 through a small additional impedance. This weak ground effectively lowers the Q of the tank circuit 2516 to widen the bandwidth for receiving telemetry signals. The receiver 2512 picks up the differential voltage between a node of the tank circuit 2516, node 2526 in this example, and ground.

During telemetry downlink, the processor/controller 202 operates the H-bridge by opening the capacitor high side switch 2530 and the inductor low side switch 2524 while the inductor high side switch 2532 and the capacitor low side switch 2522 are closed. Switches 2540 and 2452 remain open during telemetry downlink. After a set amount of time defined by the telemetry frequency, the inductor high side switch 2532 and the capacitor low side switch 2522 are opened while the capacitor high side switch 2530 and the inductor low side switch 2524 are closed. These pairings continue to alternate states to ring up the coil 2504 at the telemetry frequency and allow it to emit for a set amount of time. The capacitor low side switch 2522 and the inductor low side switch 2524 are then closed to ring down the coil 2504, which remains off for a set period until time to again ring up the coil 2504. In this manner, a carrier on/off protocol can be effectively implemented to downlink data. As an alternative, the coil 2504 may be allowed to ring down by closing a tank switch that may be included across the tank circuit 2516, by closing switches 2522 and 2524 and/or switches 2540, 2542, or by opening all switches and allowing the tank to ring down at its natural frequency.

Figure 26:
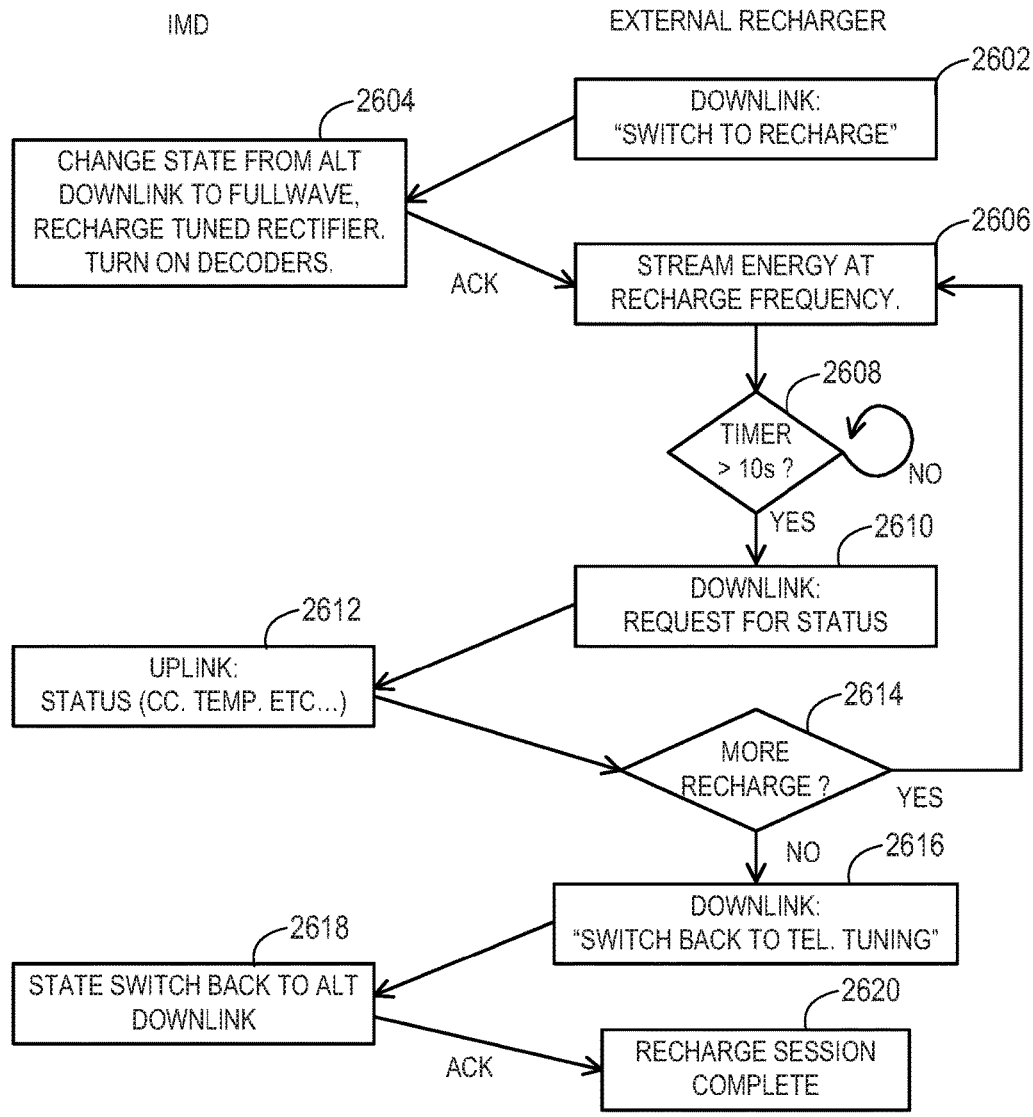
FIG. 26 shows an example of logical operations that may be performed by an external recharge device and an implantable medical device that are interacting by exchanging recharge energy and telemetry signals.

FIG. 26 shows an example of logical operations that may be performed by the external recharge device 102' and the IMD 108 when conducting recharge and telemetry during a recharge period. Initially, the IMD 108 of this example may be in a default state where the tank circuit of the IMD 108 is tuned to the telemetry frequency so that the IMD 108 may exchange telemetry with an external telemetry device 101. The external recharge device 102' downlinks an instruction at the telemetry frequency to switch to recharge frequency tuning at a downlink operation 2602 that begins the recharge period. The IMD 108 receives and implements the instruction to change the state from the telemetry frequency tuning, i.e. arm's length tuning (ALT), to recharge frequency tuning and turns on the receiver decoders at a tuning operation 2604. The IMD 108 may also uplink an acknowledgement (ACK) to the external recharge device 102' at the telemetry frequency with the tank circuit tuned to the recharge frequency.

The external recharge device 102' then begins to stream recharge energy at the recharge frequency at a recharge operation 2606. The external recharge device 102' then begins detecting whether a set period of time, such as ten seconds, has expired at a query operation 2608. If the set period of time has not expired, then the external device 102' continues to stream the recharge energy. If the set period of time has expired, then the external device 102' downlinks a request for recharge related status information at the telemetry frequency at a downlink operation 2610. Because the IMD 108 is capable of receiving the downlink at the telemetry frequency while the tank circuit of the IMD 108 is tuned to the recharge frequency, there is no need to use a timing guardband and/or handshake to establish telemetry communications because the IMD 108 may be continuously monitoring for telemetry communications while the recharge energy is streaming. Thus, the IMD 108 receives the request from the external recharge device 102' and then uplinks the status information, such as coulomb counter (cc) information, temperature, and the like using the telemetry frequency while the tank circuit is tuned to the recharge frequency at an uplink operation 2616.

The external recharge device 102' receives the uplink of status information and then detects from that information whether more recharge is needed at a query operation 2614. If more recharge is needed, then the external recharge device 102' initiates the streaming of recharge energy at the recharge operation 2606. The IMD 108 continues to be in a recharge state where the tank circuit is tuned to the recharge frequency such that when the streaming of recharge energy resumes, the IMD 108 immediately receives and rectifies the recharge energy to recharge the battery. If more recharge is not needed, then the external recharge device 102' downlinks an instruction to switch to telemetry tuning to the IMD 108 using the telemetry frequency. The IMD 108 receives and implements the instruction to tune the tank circuit to the telemetry frequency for ALT at a tuning operation 2618. The IMD 108 may also turn off the decoders of the receiver and may also uplink an ACK using the telemetry frequency. The external recharge device 102' receives the ACK and then terminates operation for the recharge session occurring during this recharge period at a completion operation 2610.

At a second time period that is prior to and/or subsequent to a first time period during which these operations of FIG. 26 are being performed, the external device 101 may initiate a telemetry session with the IMD 108. In this example, the IMD 108 is already tuned to the telemetry signal prior to and subsequent to the operations of FIG. 26 such that the IMD 108 is ready to begin the telemetry session upon request by the external device 101. Thus, when the external device 101 communicates with the IMD 108, the IMD 108 has the tank circuit tuned to the telemetry frequency which will provide maximum signal coupling between the two devices and which may allow for arm's length telemetry.

While embodiments have been particularly shown and described, it will be understood by those skilled in the art that various other changes in the form and details may be made therein without departing from the spirit and scope of the invention.

What is claimed is:

1. A method of interaction with an implantable medical device, comprising:
   while a telemetry receiver of the implantable medical device that is coupled to a tank circuit is powered on, starting to receive energy at a first frequency from the tank circuit of the implantable medical device that is tuned to the first frequency where the energy powers the implantable medical device; and
   at the implantable medical device exchanging telemetry signals at a second frequency that is different from the first frequency through the tank circuit of the implantable medical device that is tuned to the first frequency.

2. The method of claim 1, further comprising:
   at an external device, sending the energy at the first frequency from a tank circuit of the external device that is tuned to the first frequency; and
   at the external device, exchanging the telemetry signals at the second frequency through the tank circuit of the external recharge device that is tuned to the first frequency.

3. The method of claim 2, further comprising:
   at the external recharge device, sending telemetry signals that include an instruction to tune the tank circuit of the implantable medical device to the first frequency;
   at the implantable medical device, receiving the telemetry signals that include the instruction through the tank circuit of the implantable medical device while the tank circuit of the implantable medical device is tuned to the second frequency; and
   in response to receiving the instruction, tuning the tank circuit to the first frequency.

4. The method of claim 2, further comprising:
   at the external recharge device, sending telemetry signals that include an instruction to tune the tank circuit of the implantable medical device to the second frequency;
   at the implantable medical device, receiving the telemetry signals that include the instruction through the tank circuit of the implantable medical device while the tank circuit of the implantable medical device is tuned to the first frequency; and
   in response to receiving the instruction, tuning the tank circuit to the second frequency.

5. The method of claim 4, further comprising:
   at an external telemetry device, sending telemetry signals at the second frequency to the implantable medical device while the tank circuit of the implantable medical device is tuned to the second frequency.

6. A method of interaction with an implantable medical device, comprising:
   while a telemetry receiver of the implantable medical device that is coupled to a tank circuit is powered on, providing energy from a rectifier that is coupled to the tank circuit, the energy being received by the tank circuit at a first frequency while the tank circuit is tuned to the first frequency and where the energy powers the implantable medical device; and
   at the implantable medical device exchanging telemetry signals at a second frequency that is different from the first frequency through the tank circuit of the implantable medical device that is tuned to the first frequency.

7. The method of claim 6, further comprising:
   at an external device, sending the energy at the first frequency from a tank circuit of the external device that is tuned to the first frequency; and
   at the external device, exchanging the telemetry signals at the second frequency through the tank circuit of the external recharge device that is tuned to the first frequency.

8. The method of claim 7, further comprising:
   at the external recharge device, sending telemetry signals that include an instruction to tune the tank circuit of the implantable medical device to the first frequency;
   at the implantable medical device, receiving the telemetry signals that include the instruction through the tank circuit of the implantable medical device while the tank circuit of the implantable medical device is tuned to the second frequency; and
   in response to receiving the instruction, tuning the tank circuit to the first frequency.

9. The method of claim 7, further comprising:
   at the external recharge device, sending telemetry signals that include an instruction to tune the tank circuit of the implantable medical device to the second frequency;
   at the implantable medical device, receiving the telemetry signals that include the instruction through the tank circuit of the implantable medical device while the tank circuit of the implantable medical device is tuned to the first frequency; and
   in response to receiving the instruction, tuning the tank circuit to the second frequency.

10. The method of claim 9, further comprising:
    at an external telemetry device, sending telemetry signals at the second frequency to the implantable medical device while the tank circuit of the implantable medical device is tuned to the second frequency.

11. An implantable medical device, comprising:
    a tank circuit tuned to a first frequency of a power signal that carries energy used to power the implantable medical device;
    a rectifier that is electrically connected to the tank circuit to provide the energy;
    medical circuitry electrically powered by the energy provided from the rectifier; and
    a receiver configured to receive telemetry signals from the tank circuit at a second frequency that is different than the first frequency while the tank circuit is tuned to the first frequency, the receiver being powered on when the rectifier begins providing the energy.

12. The implantable medical device of claim 11, wherein the receiver receives the telemetry signals that include an instruction to begin receiving the power signals through the tank circuit and in response to receiving the instruction, tuning the tank circuit to the first frequency.

13. The implantable medical device of claim 12, wherein an acknowledgement is sent from the tank circuit in response to the receiver receiving the telemetry signals that include the instruction to begin receiving the power signals.

14. The implantable medical device of claim 11, wherein the receiver receives the telemetry signals that include an instruction to tune the tank circuit to the second frequency while the tank circuit is tuned to the first frequency and in response to receiving the instruction, tuning the tank circuit to the second frequency.

15. The implantable medical device of claim 14, wherein an acknowledgement is sent from the tank circuit in response to the receiver receiving the telemetry signals that include the instruction to tune the tank circuit to the second frequency.

16. The implantable medical device of claim 11, further comprising a controller that tunes the tank circuit.

17. The implantable medical device of claim 11, further comprising a battery coupled to the rectifier.

18. The implantable medical device of claim 11, wherein there is continuous monitoring for received telemetry signals at the receiver while the tank circuit receives the energy while being tuned to the first frequency.

19. The implantable medical device of claim 18, wherein received telemetry signals at the second frequency are received through the tank circuit while tuned to the first frequency after a period of time from when the tank circuit begins receiving energy, the received telemetry signals requesting status information.

20. The implantable medical device of claim 19, wherein sent telemetry signals at the second frequency are sent from the tank circuit while tuned to the first frequency to provide the status information.

* * * * *